(12) United States Patent
Dalhoff et al.

(10) Patent No.: US 11,786,149 B2
(45) Date of Patent: Oct. 17, 2023

(54) METHOD AND APPARATUS FOR TESTING HEARING ABILITY

(71) Applicant: Eberhard Karls University Tübingen, Tübingen (DE)

(72) Inventors: Ernst Dalhoff, Rottenburg (DE); Dennis Zelle, Tübingen (DE)

(73) Assignee: Eberhard Karls University Tübingen, Tübingen (DE)

( * ) Notice: Subject to any disclaimer, the term of this patent is extended or adjusted under 35 U.S.C. 154(b) by 605 days.

(21) Appl. No.: 16/623,091

(22) PCT Filed: Jun. 15, 2018

(86) PCT No.: PCT/EP2018/066033
§ 371 (c)(1),
(2) Date: Dec. 16, 2019

(87) PCT Pub. No.: WO2018/229287
PCT Pub. Date: Dec. 20, 2018

(65) Prior Publication Data
US 2020/0268288 A1 Aug. 27, 2020

(30) Foreign Application Priority Data
Jun. 16, 2017 (DE) .......................... 102017005675.7

(51) Int. Cl.
*A61B 5/12* (2006.01)
*A61B 5/00* (2006.01)
(Continued)

(52) U.S. Cl.
CPC ............ *A61B 5/125* (2013.01); *A61B 5/6817* (2013.01); *A61B 5/7203* (2013.01); *H04R 1/26* (2013.01); *H04R 25/70* (2013.01)

(58) Field of Classification Search
CPC ..... A61B 5/125; A61B 5/6817; A61B 5/7203; A61B 5/7235; A61B 5/7271; H04R 1/26; H04R 25/70
See application file for complete search history.

(56) References Cited

U.S. PATENT DOCUMENTS 5,885,225 A 3/1999 Keefe
11,024,421 B2 6/2021 Dalhoff et al.
(Continued)

FOREIGN PATENT DOCUMENTS

DE 69738629 T2 5/2009
DE 102011121686 A1 6/2013
(Continued)

OTHER PUBLICATIONS

Kim, D.O. et al. "A New Method of Measuring Distortion Product Otoacoustic Emissions Using Multiple Tone Pairs: Study of Human Adults" 1997, Ear and Hearing, vol. 18 (4), pp. 277-285 (Year: 1997).*
(Continued)

*Primary Examiner* — Alex M Valvis
*Assistant Examiner* — Anna Roberts
(74) *Attorney, Agent, or Firm* — Workman Nydegger

(57) ABSTRACT

The present invention concerns a method for the detection of distortion products of otoacoustic emissions (DPOAE), comprising the steps: (a) output of at least one first pair of primary tones each consisting of a first primary tone with frequency $f_{1,1}$ and sound pressure level $L_{1,1}$ and a second primary tone with frequency $f_{2,1}$ and sound pressure level $L_{2,1}$ with $f_{2,1} > f_{1,1}$, and (b) detecting evoked distortion products of otoacoustic emissions (DPOAE), characterized in that the first primary tone $\{f_{1,1}, L_{1,1}\}$ is output with a time delay $t_{lag}$ after the second primary tone $\{f_{2,1}, L_{2,1}\}$.

19 Claims, 10 Drawing Sheets

Figure 1:
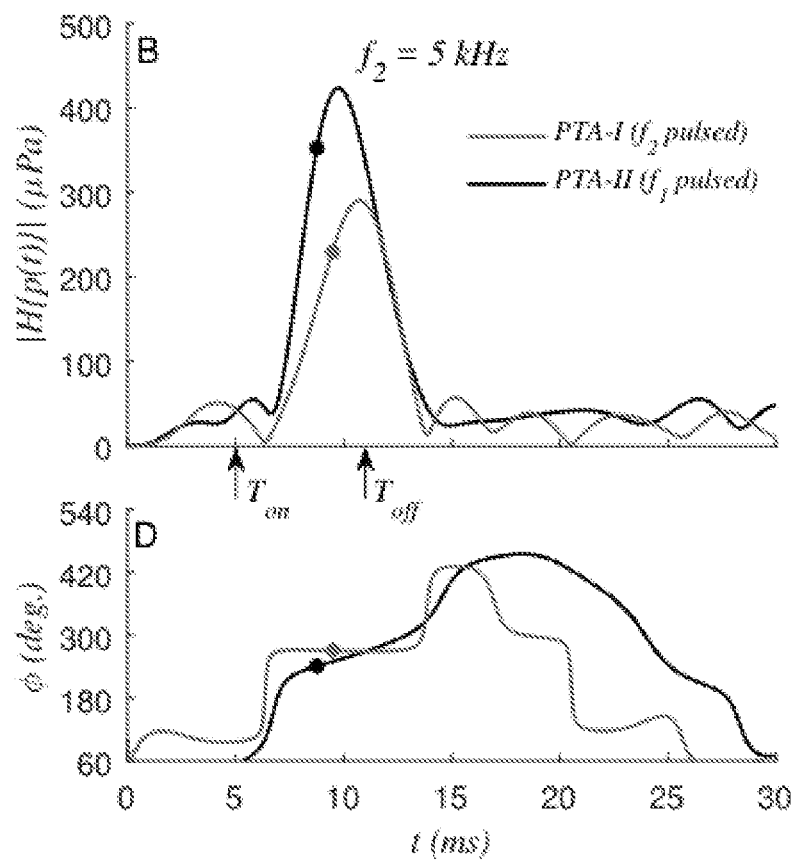

(51) Int. Cl.
*H04R 1/26* (2006.01)
*H04R 25/00* (2006.01)

(56) References Cited

U.S. PATENT DOCUMENTS

| 2014/0114209 | A1 | 4/2014 | Lodwig |
| 2016/0183849 | A1 | 6/2016 | Rembrand |
| 2017/0150908 | A1* | 6/2017 | Nadon .................... A61F 11/08 |
| 2017/0150909 | A1* | 6/2017 | Dalhoff ................ A61B 5/6817 |

FOREIGN PATENT DOCUMENTS

| DE | 102016003133 | | 9/2017 | |
| EP | 1027863 | A1 | 8/2000 | |
| EP | 2053877 | A1 | 4/2009 | |
| WO | 2015192969 | | 12/2015 | |
| WO | WO-2015192969 | A1 * | 12/2015 | ............. A61B 5/125 |

OTHER PUBLICATIONS

Dalhoff, Ernst, et al. "Two-source interference as the major reason for auditory-threshold estimation error based on DPOAE inputeoutput functions in normal-hearing subjects" 2013, Hearing Research, 296, 67-82 (Year: 2013).*

Whitehead et al., "Dependence of distortion-product otoacoustic emissions on primary levels in normal and impaired ears. II. Assymetry in L 1, L 2 space", The Journal of the Acoustical Society of America, Bd. 97, Nr. 4, Apr. 1, 1995, Seiten 2359-2377, XP055378625.

Zelle D. et al., "Level dependence of the nonlinear-distortion component of distortion-product otoacoustic emissions in humans", The journal of the Acoustical society of America, American Institute of physics for the acoustical society of America, NY, US, Bd. 138, Nr. 6, Dec. 8, 2015, Seiten 3475-3490, XPO142203260.

Zelle, D., et al.; "Objective Audiometry with DPOAEs"; Section of Physiological Acoustics and Communication, Department of Otolaryngology, University of Tubingen; May 3, 2017; pp. S122-S129; HNO 2017-65—Suppl 2; Tubingen, Germany.

Buckley, Jay et al. "DPOAE level mapping for detecting noise-induced cochlear damage from short-duration music exposures", Noise and Health, vol. 17, Issue 78, Sep. 2015.

Dalhoff E. et al, Two-source interference as the major reason for auditory-threshold estimation error based on DPOAE input-output functions in normal-hearing subjects, Hear Res. Feb. 2013;296:67-82. doi: 10.1016/j.heares.2012.12.003. EpubDec. 23, 2012.

Dhar Sumitrajit, et al: "The effect of stimulus-frequency ratio on distortion product otoacoustic emission components", The Journal of the Acoustical Society of America, Bd. 117, 2005, Seiten 3766-3776.

Mills, David M. et al: "Interpretation of distortion product otoacoustic emission measurements", The Journal of the Acoustical Society of America 102, 413 (1997).

Salata, et al: "Distortion-product otoacoustic emissions hearing-screening in high-risk newborns", Otolaryngology and head and neck surgery, US, Bd. 118, 1998, Seiten 37-43.

* cited by examiner

METHOD AND APPARATUS FOR TESTING HEARING ABILITY

The invention concerns a method based on the measurement of distortion products of otoacoustic emissions (DPOAE). The procedure according to the invention serves in particular for the objective and quantitative determination of the sound processing in a mammalian ear and thus for the examination and subsequent evaluation of the hearing ability. According to EP 2 053 877 A1 and DE 199 05 743 A1, the measurement results can also be used to adjust hearing aids. The method is based on a special excitation pattern which allows conclusions to be drawn about the operating point of the cochlear amplifier.

In particular, this invention concerns a method for detecting distortion products of otoacoustic emissions (DPOAE) in a hearing organ, comprising the steps: (a) output of at least one first pair of primary tones each consisting of a first primary tone with frequency $f_{1,1}$ and sound pressure level $L_{1,1}$ and a second primary tone with frequency $f_{2,1}$ and sound pressure level $L_{2,1}$ with $f_{2,1} > f_{1,1}$, and (b) detecting evoked distortion product otoacoustic emissions (DPOAE), characterized in that the first primary tone $\{f_{1,1}, L_{1,1}\}$ is output with a time delay $t_{lag}$ after the second primary tone $\{f_{2,1}, L_{2,1}\}$.

The hearing pathway can be seen as a chain of successive signal processing blocks. These are passed through before the more complex perception of hearing arises in the cortex. The first blocks of the signal processing chain are the outer ear (auricle & ear canal), the middle ear (middle-ear ossicles comprising stapes footplate as the boundary to the inner-ear fluids), and the fluid-filled inner ear. The vast majority of hearing damage occurs in the inner ear. This also includes age-related hearing loss, which on average leads to 25 dB hearing loss in women at the age of 60-70 years and 35 dB in men in the frequency range above 4 kHz. It is dominated by an impairment of the so-called cochlear amplifier, which in a healthy state amplifies the incoming sound waves by a factor of 300-1000 before they are converted into neural signals by the inner hair cells and their synapses.

The existence of the cochlear amplifier has been successively proven since about 1980, and the discovery of the otoacoustic emissions (OAEs) by David T. Kemp played a central role in this. These are sounds generated by the (cochlear) active amplifier as a by-product and transmitted backwards through the middle ear to the auditory canal. There they can be measured with sensitive miniature microphones.

One form of OAE are distortion product otoacoustic emissions (DPOAE), which are typically evoked by the simultaneous presentation of two primary tones at the frequencies $f_1$ and $f_2$ and the sound pressure levels $L_1$ and $L_2$. The nonlinear characteristic of the mechanoelectric transduction of the ion channels of the outer hair cells, which are the main motor element of the cochlear amplifier in humans and mammals in general, leads to numerous distortion products. The most easily measurable distortion product and therefore preferred in diagnostic applications is that at $f_{dp} = 2f_1 - f_2$ with $f_2 > f_1$ and an optimal frequency ratio of about $$\frac{f_2}{f_1} = 1.2.$$

With suitable selection of the stimulus parameters (preferably $$\frac{f_2}{f_1} = 1.2$$

and $L_1 \geq L_2$) the travelling waves evoked by the primary tones overlap in the cochlea in a basal region to the characteristic place of frequency $f_2$. Nowadays DPOAE are usually evoked in such a way that at the characteristic place of the second primary tone both excitation frequencies lead to oscillation amplitudes of the basilar membrane of possibly equal amplitude, and accordingly diagnostic conclusions from DPOAE findings are interpreted with respect to frequency and excitation level of the second primary tone $\{f_2, L_2\}$. DPOAE measurements can, for example, be performed and interpreted at different frequencies according to the procedure described in DE 102014108663.

As a rule, the amplitude of the DPOAE is extracted from the spectrum of the measured signal using a Fourier transform. Since the DPOAE have a very low sound pressure level, which can be well below the hearing threshold, a sufficiently long average must be taken to obtain a certain signal-to-noise ratio and thus a reliable diagnostic result. If several DPOAEs measured at a frequency $f_2$ and different sound pressure levels $L_2$ are combined to form a so-called growth function, a more precise statement can be made about the function of the cochlear amplifier in the inner ear. For each excitation frequency $f_2$, the so-called threshold value can then be determined on the basis of the growth function, by which the lowest level $L_2$ is understood, at which the DPOAE still reaches a given minimum signal-to-noise ratio. Or, the threshold can be determined by extrapolation of the growth function in order to become independent on the finite noise background.

In order to obtain a diagnostic statement over the entire frequency range, 6 to 8 growth functions are typically measured sequentially.

The growth curves thus determined and the extrapolated thresholds can then serve as a basis for improved diagnostics and for the adjustment of hearing aids, because the extrapolated thresholds can be regarded as a direct indicator of hearing loss.

The generation process of DPOAE and the measurement and evaluation methods used so far are also described in Dalhoff et al., "Sound and velocity DPOAE", in HNO 2010, 58: 543-555. There, additional references are given to which explicit reference is made.

The excitation of the DPOAE can basically be done by continuous tones as well as by pulsed tones. As mentioned earlier, continuous tones are those tones that are presented for so long that their spectrum is sharp.

With the pulsed DPOAE at least one of the two primary tones (typically the second primary tone $\{f_2, L_2\}$) is presented pulsed, while the other primary tone (typically the first primary tone $\{f_1, L_1\}$) is also pulsed or presented as a continuous tone. The ratio of $L_2$ to $L_1$ is first set in a certain range, then $L_2$ is changed step by step. According to the general Fourier relationship between time domain and frequency domain, the "pulsed (primary) tones" are tones whose spectrum is broadened due to the brevity of the pulse. If one of the tones, e.g. the aforementioned first primary tone $\{f_1, L_1\}$, is presented as a continuous tone, this means that the pulsed second primary tone $\{f_2, L_2\}$ is switched on and off during the uninterrupted presentation of the first primary tone $\{f_1, L_1\}$. Conversely, the second primary tone $\{f_2, L_2\}$ can also be presented as a continuous tone, while the pulsed first primary tone $\{f_1, L_1\}$ undergoes a switch-on and switch-off process during the uninterrupted presentation of the second primary tone $\{f_2, L_2\}$.

Methods of pulsed DPOAE are among others described in Dalhoff et al., "Two-source interference as the major reason for auditory-threshold estimation error based on DPOAE input-output functions in normal-hearing subjects", in Hearing Research 296 (2013), pages 67-82. Another method of pulsed DPOAE with pulse interlacing is disclosed in WO 2015/192969 A1.

In the process described in WO 2015/102969 A1, a first pulsed primary tone $\{f_{1,1}, L_{1,1}\}$ and a second pulsed primary tone $\{f_{2,1}, L_{2,1}\}$ are applied, the $f_1$-pulse starting before the $f_2$-pulse and ending after the $f_2$-pulse, i.e. the $f_1$-pulse being longer than the $f_2$-pulse of a pulse pair. WO 2015/102969 A1 refers to short pulses of approximately 1-10 ms, the duration of which corresponds approximately to the latency between stimulation and the development of the first nonlinear distortion contribution of a DPOAE on the basilar membrane in the inner ear. In an alternative design described in WO 2015/102969 A1, two short pulses of the same or similar length are finally presented in which the $f_1$-pulse begins after the $f_2$-pulse. To save time, these two short pulses are adjusted so that both pulses arrive simultaneously at the $f_2$-characteristic place in the inner ear.

All known DPOAE methods (including the pulsed DPOAE described above) are used to diagnose the amplification power of the cochlear amplifier, which, together with the outer hair cells (OHC) as key elements, is responsible for mechanical pre-neural amplification of the input signal, and thus also determines the hearing threshold up to a hearing loss of about 50 to 60 dB (D. Zelle, E. Dalhoff, and A. W. Gummer, "Objective Hearing Diagnostics with DPOAE. New findings on generation and clinical application," HNO, vol. 64, no. 11, pp. 822-830, 2016). However, it has not yet been possible to determine the cause of cochlear gain loss using the known methods, in particular whether it is due to a loss of intact OHC, or rather an impairment of the energy supply caused by the stria vascularis (i.e. ultimately a reduction of the endocochlear potential).

This is the starting point for the further development of the method according to the present invention which has the task of providing a DPOAE method which can improve the known DPOAE methods and which, in particular, can provide information about the cause of a gain loss.

According to the invention, if one uses the above-mentioned method (WO 2015/102969 A1), this task is solved by presenting a pair of two primary tones with excitation frequencies $f_1$ and $f_2$, where the second primary tone $\{f_2, L_2\}$, being excited in accordance with the usual excitation paradigms with a significantly lower sound pressure, is presented first, while the first primary tone $\{f_1, L_1\}$ is presented with a time delay $t_{lag}$ with respect to the second primary tone $\{f_2, L_2\}$.

The first primary tone is defined by a first excitation frequency $f_1$ and a first sound pressure level $L_1$. It is also known as the "$f_1$-primary tone". The second primary tone is defined by a first excitation frequency $f_2$ and a first sound pressure level $L_2$. It is also known as the "$f_2$-primary tone". If in the following we talk about a "first primary tone $\{f_1, L_1\}$" or a "$f_1$-primary tone", the corresponding explanations basically refer both to the first primary tone of the first primary-tone pair of the method according to the invention (i.e. the first primary tone $\{f_{1,1}, L_{1,1}\}$) and to each further first primary tone of an n-th (further) primary-tone pair (i.e. the first primary tone $\{f_{1,n}, L_{1,n}\}$). Analogously the term "second primary tone $\{f_2, L_2\}$" or "$f_1$-primary tone" basically includes the second primary tone $\{f_{2,1}, L_{2,1}\}$, as well as every further second primary tone of an n-th (further) primary-tone pair (i.e. the second primary tone $\{f_{2,n}, L_{2,n}\}$).

The time delay $t_{lag}$ until the first primary tone $\{f_1, L_1\}$ is presented typically depends on the latencies of the two travelling waves involved. Latency functions for the non-linear source are given in D. Zelle, A. W. Gummer, and E. Dalhoff, "Latencies of Extracted Distortion-Product Otoacoustic Source Components," in Mechanics of Hearing: Protein to Perception, vol. 1703, K. D. Karavitaki and D. P. Corey, Eds.: AIP conference proceedings, 2014.

Preferably $t_{lag}$ is at least 0.5 milliseconds (ms), i.e. the first, preferably pulsed, primary tone $\{f_1, L_1\}$ is preferably switched on at least 0.5 ms after the second primary tone $\{f_2, L_2\}$. In principle, $t_{lag}$ can be selected as large as desired, but it can be advantageous to keep the time delay $t_{lag}$ as short as possible in order not to unnecessarily extend the measurement time. Therefore, $t_{lag}$ is preferably selected less than or equal to 10 ms, less than or equal to 7.5 ms or particularly preferred less than or equal to 5 ms. Preferred is $t_{lag}$ selected from the range between 10 ms and 0 ms, particularly preferred from the range between 5 ms and 0.5 ms.

The first primary tone $\{f_{1,1}, L_{1,1}\}$ is preferably presented pulsed (i.e. as "$f_1$-pulse"). As indicated above, "pulsed" primary tones are tones which, according to the general Fourier relationship between time domain and frequency domain, have a broader spectrum due to the brevity of the pulse. Furthermore, the second primary tone $\{f_{2,1}, L_{2,1}\}$ can be pulsed (i.e. as "$f_2$-pulse") or presented as a continuous tone. "Pulsed" primary tones undergo a turn-on and turn-off process during the measurement period and are typically presented for a duration of 50 ms or less. In the method according to the invention, the second primary tone $\{f_{2,1}, L_{2,1}\}$ is presented as a continuous tone or pulsed ("$f_2$-pulse"), while the first primary tone $\{f_{1,1}, L_{1,1}\}$ is preferably presented pulsed ("$f_1$-pulse"). Preferably, both primary tones are presented pulsed, the pulse length of the second primary tone $\{f_{2,1}, L_{2,1}\}$ exceeding the pulse length of the first primary tone $\{f_{1,1}, L_{1,1}\}$.

Furthermore, regardless of the type of presentation of the second primary tone as a continuous tone or pulse, it may be preferred that the $f_1$-pulse undergoes a switch-on and switch-off process during the uninterrupted presentation of the second primary tone $\{f_{2,1}, L_{2,1}\}$. If both primary tones of the primary-tone pair are presented in pulses (in other words: as $f_1$-pulse or the $f_2$-pulse), it may be preferred that the pulse length of the $f_1$-pulse is shorter than the pulse length of the $f_2$-pulse.

Alternatively, when both primary tones are pulsed, the second pulsed primary tone $\{f_{2,1}, L_{2,1}\}$ can be switched on first, whereas the first pulsed primary tone $\{f_{1,1}, L_{1,1}\}$ is presented with a time delay $t_{lag}$ (as defined above) and switched off after the second pulsed primary tone $\{f_{2,1}, L_{2,1}\}$. This procedure can also be considered as a mixture of the excitation schemes of PTA-I and PTA-II. The presentation takes place after switching on according to PTA-II. Preferably, the DPOAE excitation according to PTA-II provides information on the correct homeostasis of the inner ear. Before switching off, the presentation is carried out according to PTA-I, whereby the interference state of the non-linear and coherent reflection source can be determined.

The $f_1$-pulse of the first primary tone pair $\{f_{1,1}, L_{1,1}; f_{2,1}, L_{2,1}\}$ can thus be switched off before or after the end of the $f_2$-pulse of the first primary-tone pair.

In any case, the duration of the $f_1$-pulse and/or the duration of the $f_2$-pulse in the PTA-II excitation scheme may be chosen to be greater than the latency of evoked DPOAE, preferably at least twice, more preferably at least three times and most preferably at least five times as long. It may be particularly preferable to select the duration of the $f_1$-pulse and/or the duration of the $f_2$-pulse in the PTA-II excitation scheme so that it corresponds to five to seven times the latency of the evoked DPOAE. The latency of evoked DPOAE depends on the selected frequency for each $f_1$ and $f_2$-primary tone (see Zelle et al. AIP Conference Proceedings 1703, 090023 (2016)).

The length of the first primary tone $\{f_{1,1}, L_{1,1}\}$ can preferably be between 40 ms and 1 ms, even more preferably between 30 ms and 2 ms, even more preferably between 25 ms and 2 ms. The length of the second primary tone $\{f_{2,1}, L_{2,1}\}$ is then selected accordingly longer. Thus, the second primary tone $\{f_{2,1}, L_{2,1}\}$ can be presented as continuous tone or pulsed. However, depending on the overall excitation pattern selected, the preferred pulse length may differ. Especially for the combined PTA-I/PTA-II excitation scheme, longer pulses of 200 ms or less, 100 ms or less, or 50 ms or less may be considered as described below.

The "duration" or "length" of a pulse (also called "pulse length" or "pulse width") is the so-called full width half maximum (or $T_{FWHM}$). For this pulse length, the time is determined from which the cosine-shaped rising edge has risen to half of the steady-state until the corresponding time in the switch-off time response. This pulse length results from the preferred pulse shape, according to which the pulses have a cosine-shaped increase of typically 0.1 ms to 4 ms in length, a steady-state with the sound pressure level $L_2$ or $L_1$, which is typically 2 ms to 12 ms long, followed by another cosine-shaped section.

The sound pressure levels $L_1$ and $L_2$ of at least one primary tone pair can preferably be selected similarly, since the risk of mutual suppression can increase with increasing sound pressure level difference. If several primary-tone pairs are presented in one measurement, a fixed threshold can be defined for the maximum sound-pressure level difference between the $L_2$ sound pressure levels of, for example, four primary-tone pairs, which can be between 5 and 15 dB, for example.

The excitation patterns described here with a time-shifted presentation (i.e. by $t_{lag}$) of the (preferably pulsed) $f_1$-primary tone are also referred to as Primary-Tone Arrangement II (PTA-II) and are in contrast to state-of-the-art methods in which the $f_1$-primary tone is presented first and the $f_2$-primary tone is presented time-shifted. Such state-of-the-art excitation patterns are also referred to here as Primary-Tone Arrangement I (PTA-I).

The inventors recognized that a DPOAE excitation according to PTA-I or PTA-II leads to different amplitudes (cf. FIG. 1). In particular, the response of the nonlinear source (i.e. the part of the envelope of the $2f_1-f_2$-DPOAE time signal that comes first in time) is greater for PTA-II than for PTA-I. This is particularly interesting because its amplitude is usually greater than that of the coherent reflection sources and, in contrast, it is not dependent on any additional process (namely the presumed roughness of the impedance function). The reason for the observed deviation with respect to the response of the nonlinear source lies in the asymmetry of the so-called mechano-electric transduction curve of the OHC. This transduction curve represents the dependence of the intracellular receptor potential (output) on the stimulus, e.g. the displacement of the stereocilia of the OHC (input). With intact cochlear homeostasis, the operating point is approximately at the point of the maximum slope of the curve (cf. simplified simulation in FIG. 2).

The excitation of the nonlinear source of the DPOAE takes place near the characteristic place of the second primary tone with the frequency $f_2$ ("$f_2$-characteristic place"), where the travelling waves of both primary tones overlap most strongly. Decisive for the generation of the DPOAE is the range from about ½ octave basal to the $f_2$-characteristic place, since here the OHC contribute maximally to the amplification of the input oscillations. At the $f_2$-characteristic place, both primary tones have different latencies, since the phase transfer function of a cochlear travelling wave becomes steeper and steeper towards its characteristic place. Therefore, the largest phase rotation takes place just before the maximum of the wave amplitude. Since the travelling wave of the first primary tone ("$f_1$-travelling wave") has not yet reached its maximum amplitude at the $f_2$-characteristic place, its latency at this location is significantly lower. If both primary tones are switched on simultaneously, the $f_1$-travelling wave will first reach the $f_2$-characteristic place and contribute to the DC potential shift before the second primary tone $\{f_2, L_2\}$ arrives and the DPOAE can be generated. This is the case in the PTA-I scheme.

When using the PTA-II scheme according to the invention—where the (pulsed) second primary tone $\{f_2, L_2\}$ is first switched on and optionally last switched off—the relatively quieter $f_2$-pulse does not yet lead to a noticeable DC potential shift, so that the pulsed first primary tone $\{f_1, L_1\}$ is presented when the cochlear amplifier is still (almost) in the idle state. In the normal physiological state of the cochlea, the operating point is close to the optimum, i.e. the highest amplification power. Thus one obtains a higher DPOAE amplitude.

It is therefore advantageous to compare two measurements, i.e. a PTA-I and a PTA-II measurement at the same frequency and the same excitation levels of the two primary tones, in order to determine whether the expected change in amplitude is present and therefore whether an optimal, non-pathological adjustment of the operating point of the cochlear amplifier can be assumed.

In the method according to the invention, the excitation takes place with at least one pair of primary tones $\{f_{1,1}, L_{1,1}\}$ and $\{f_{1,2}, L_{2,1}\}$ which are preferably both presented in pulsed form (i.e. as a "pair of pulses").

The excitation frequencies $f_1$ and $f_2$ of a primary-tone pair are preferably related by a frequency ratio $f_2/f_1=1.2$. Deviating from this, however, this frequency ratio can also be set to any other suitable value, preferably between 1.15 and 1.35, see e.g. Johnson et al. "Influence of primary-level and primary-frequency ratios on human distortion product otoacoustic emissions", in J. Acoust. Soc. Am. 119, 2006, pages 418-428.

Such primary-tone pairs usually consist of a first (pulsed) and a second (optionally pulsed) primary tone $\{f_1, L_1\}$ and $\{f_2, L_2\}$, where the frequency $f_1$ is determined from $f_2$ using a defined frequency ratio. The sound pressure level $L_1$ can also be calculated from $L_2$ according to a predefined rule. The term "primary-tone pair" includes the term "pair of pulses" which means a pair of first pulsed and second pulsed primary tone $\{f_1, L_1\}$ and $\{f_2, L_2\}$.

As described above, according to the invention the first and the second primary tone of a primary-tones pair are presented in a slightly time-shifted manner, whereby the (preferably pulsed) second primary tone $\{f_{2,1}, L_{2,1}\}$ precedes the (preferably pulsed) first primary tone $\{f_{1,1}, L_{1,1}\}$. If the (preferably pulsed) first primary tone $\{f_{1,1}, L_{1,1}\}$ ends before the (preferably pulsed) second primary tone, and in particular if the first primary tone $\{f_{1,1}, L_{1,1}\}$ has a shorter pulse length than the second primary tone $\{f_{2,1}, L_{2,1}\}$ in the pulsed presentation of both primary tones, this excitation scheme is also referred to as "PTA-II". On the other hand, an excitation scheme in which a (preferably pulsed) first primary tone $\{f_{1,n}, L_{1,n}\}$ starts before the (preferably pulsed) second primary tone $\{f_{2,n}, L_{2,n}\}$ and ends after this, in particular if, in the case of pulsed presentation of both primary tones, the second primary tone $\{f_{2,n}, L_{2,n}\}$ has a shorter pulse length than the first primary tone $\{f_{1,n}, L_{1,n}\}$, it is referred to as "PTA-I". Typical pulse lengths are mentioned above and are basically applicable to PTA-I and PTA-II.

Figure 3:
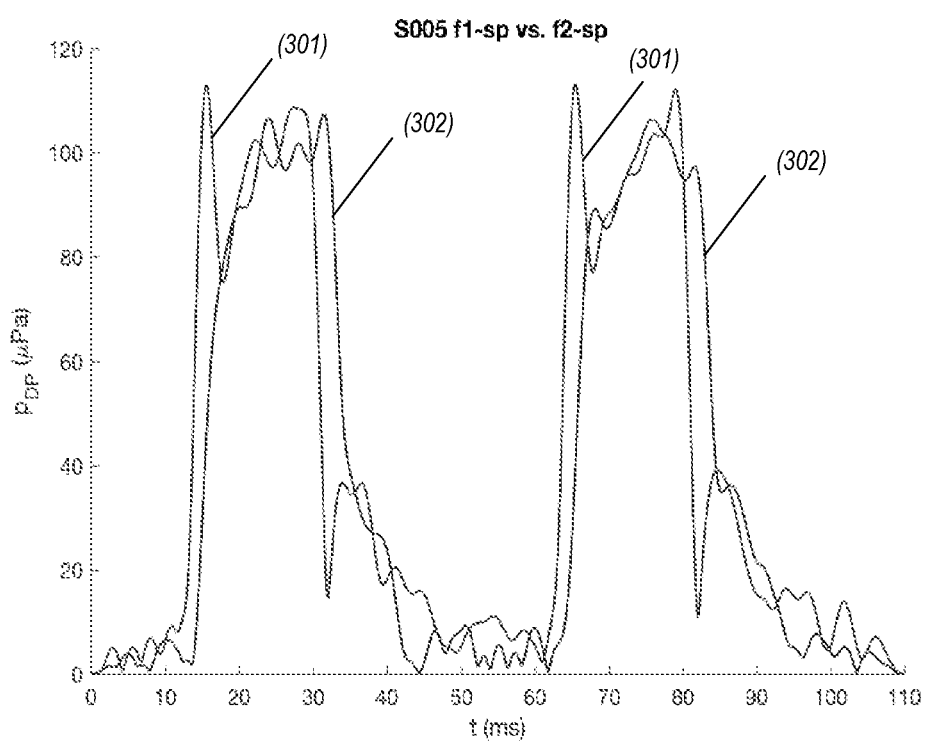

According to the invention, it may be preferable to extend the length of the $f_1$-pulse beyond the latency of the nonlinear source ("extended $f_1$-pulse") in order to preferably show the stimulus-induced shift of the receptor potential in a single measurement (cf. FIG. 3). Typical pulse lengths for extended $f_1$-pulse are preferably between 5 and 20 ms.

As described above, in the inventive procedure the $f_2$-primary tone of a primary-tone pair begins before the (preferably pulsed) $f_1$-primary tone begins, and can end after the (pulsed) $f_1$-primary tone has been terminated, i.e. the $f_2$-primary tone can last longer than the (pulsed) $f_1$-primary tone of a primary-tone pair. If the $f_1$-primary tone is switched on with a time delay tlag relative to the $f_2$-primary tone, the DPOAE preferably reaches a maximum at the beginning and then drops to rise again (see FIG. 3). This subsequent increase can in principle be caused by the influence of the second source (reflection component), but also by slower control processes of the difference between intra- and extracellular potentials, or by the dynamics of the locally limited positive feedback loop, which leads to cochlear amplification.

When the (preferably pulsed) $f_1$-primary tone is switched off, a recovery process takes place, which in principle can result both from the restoration of the resting potential and from influences of the second, i.e. the coherent reflection source.

In state-of-the-art methods with an excitation according to PTA-I, however, neither the early maximum nor the recovery process is reached after switching off the (typically pulsed) $f_2$-primary tone. On the other hand, a single measurement according to the method of the invention with a (preferably pulsed) $f_1$-primary tone can already clarify the presence of a DC potential shift. If there is a pathological shift of the DC potential, the change is expected to be significantly smaller depending on the frequency, and under certain circumstances (e.g. at low frequencies) even the sign may change.

Alternatively, in the procedure according to the invention, the $f_2$-primary tone of a primary-tone pair starts before the (preferably pulsed) $f_1$-primary tone starts, and can end before the $f_1$-primary tone has been terminated. In other words, the $f_1$-pulse ends after the $f_2$-pulse is switched off.

The method in accordance with the invention may also include the output of at least one further (n-th) pair of primary tones, each consisting of a first primary tone with frequency $f_{1,n}$ and sound pressure level $L_{1,n}$ and a second primary tone with frequency $f_{2,n}$ and sound pressure level $L_{2,n}$, where $f_{2,n} > f_{1,n}$. The other pair of primary tones has an $f_2$-excitation frequency which is either different from the $f_2$-excitation frequency of the first pair of primary tones (i.e. $f_{2,1} \neq f_{2,n}$) or an $f_2$-excitation frequency which corresponds to the $f_2$-excitation frequency of the first pair of primary tones (i.e. $f_{2,1} = f_{2,n}$). The presentation of at least one additional pair of primary tones can be made either before or after the presentation of the first pair of primary tones. It is also possible that the presentation of the first pair of primary tones is "embedded" in the presentation of further pairs of primary tones.

The at least one additional primary-tone pair can be presented according to the excitation pattern PTA-II (like the first primary-tone pair) or according to the excitation pattern PTA-I. This means that (a) the second primary tone of the at least one further primary tone pair $\{f_{2,n}, L_{2n}\}$ can be presented with a time delay $t_{lag}$ after the first primary tone $\{f_{1,n}, L_{1,n}\}$ of this at least one further primary-tone pair with a time delay $t_{lag}$, or (b) the first primary tone of the at least one further primary-tone pair $\{f_{1,n}, L_{1,n}\}$ can be output with a time delay $t_{lag}$ after the second primary tone $\{f_{2,n}, L_{2,n}\}$ of this at least one further primary-tone pair with a time delay $t_{lag}$ after the second primary tone $\{f_{2,n}, L_{2,n}\}$ of this at least one further primary tone pair.

The number of primary-tone pairs n can be selected from any number, preferably a whole number ≥2. Preferably n=2.

Here option (a) preferably corresponds to an excitation according to PTA-I. In particular, it is envisaged to present the second primary tone and optionally the first primary tone in pulsed form. If both primary tones are presented pulsed, the pulse length of the $f_2$ pulse may preferably be shorter than the pulse length of the $f_1$ pulse.

Option (b) preferably corresponds to an excitation according to PTA-II. In particular, it is envisaged to present the first primary tone and optionally the second primary tone in pulsed form. If both primary tones are presented pulsed, the pulse length of the $f_1$-pulse may preferably be shorter than the pulse length of the $f_2$-pulse.

As described above, a combined PTA-I/PTA-II excitation scheme is particularly useful to compare the change in amplitude of the excited DPOAE (especially the nonlinear source). For this purpose at least one further n-th primary-tone pair $\{f_{1,n}, L_{1,n}, f_{2,n}, L_{2,n}\}$ is presented preferably after the excitation according to the invention according to the PTA-II scheme, wherein the second primary tone $\{f_{2,n}, L_{2n}\}$ of the at least one further n-th primary-tone pair is presented with a time delay $t_{lag}$ after the first primary tone $\{f_{1,n}, L_{1,n}\}$ of this primary-tone pair. The output of the at least one further n-th primary-tone pair $\{f_{1,n}, L_{1,n}, f_{2,n}, L_{2n}\}$ can optionally take place before or after the output of the first primary tone pair $\{f_{1,1}, L_{1,1}, f_{2,1}, L_{2,1}\}$.

The method according to the invention may preferably—especially if it includes stimulation by means of PTA-I and PTA-II—comprise further a step of comparison of the results obtained by output of the first primary-tone pair $\{f_{1,1}, L_{1,1}, f_{2,1}, L_{2,1}\}$ with those evoked by the output of a further primary-tone pair $\{f_{1,n}, L_{1,n}, f_{2,n}, L_{2,n}\}$ with identical sound pressure levels L and frequencies f but different delay between the stimulus pulses.

As described above, the first primary tone $\{f_{1,1}, L_{1,1}\}$ and/or $\{f_{1,n}, L_{1,n}\}$ and optionally the second primary tone $\{f_{2,1}, L_{2,1}\}$ and/or $\{f_{2,n}, L_{2,n}\}$ can be presented according to the invention preferably pulsed, i.e. as "$f_1$-pulse" or "$f_2$-pulse", respectively. This applies to an excitation according to PTA-II as well as to a possible additional excitation according to PTA-I.

For the preferred excitation frequencies, sound pressure levels, pulse lengths and other parameters for excitation in accordance with PTA-I, the designs with respect to PTA-II apply accordingly.

In particular, the duration of the $f_1$-pulse and/or the duration of the $f_2$-pulse in the PTA-I excitation scheme may be chosen to be greater than the latency of evoked DPOAE, preferably at least twice, more preferably at least three times and most preferably at least five times as long. It may be particularly preferable to select the duration of the $f_1$-pulse and/or the duration of the $f_2$-pulse in the PTA-I excitation scheme so that it corresponds to five to seven times the latency of the evoked DPOAE.

In particular, the duration of the $f_1$-pulse $\{f_{1,1}, L_{1,1}\}$ of the first primary-tone pair and/or of the $f_2$-pulse $\{f_{2,n}, L_{2,n}\}$ of the n-th further primary-tone pair may be 200 ms or less, 100 ms or less, 50 ms or less, between 40 ms to 1 ms, between 30 ms and 2 ms or between 25 ms and 5 ms. Especially for a combined PTA-I/PTA-II excitation scheme, the pulse length can be extended to 200 ms or less, 100 ms or less, or 50 ms or less. Furthermore, the pulse length of the $f_2$-pulse of the n-th further primary-tone pair $\{f_{2,n}, L_{2,n}\}$ can preferably be shorter than the pulse length of the $f_1$-pulse of the n-th further primary-tone pair $\{f_{1,n}, L_{1,n}\}$.

As explained above, the combination of an excitation according to PTA-II with the first primary-tone pair $\{f_{1,1}, L_{1,1}, f_{2,1}, L_{2,1}\}$ with an excitation according to PTA-I with a second primary-tone pair $\{f_{1,n}, L_{1,n}, f_{2,n}, L_{2,n}\}$ can be advantageous to compare the obtained amplitudes with each other and to draw conclusions about the adjustment of the operating point of the cochlear amplifier. For this purpose, the excitation frequencies and sound pressure levels are chosen the same, and only the respective excitation scheme is changed in order to guarantee the comparability of the obtained results. In other words, the frequency and sound pressure level of the first primary tone of the first and each subsequent n-th primary-tone pair and/or the frequency and sound pressure level of the second primary tone of the first and each subsequent n-th primary-tone pair are preferably identical. To put it another way, the following applies preferentially in the methods according to the invention: $\{f_{1,1}, L_{1,1}\}=\{f_{1,n}, L_{1,n}\}$ and/or $\{f_{2,1}, L_{2,1}\}=\{f_{2,n}, L_{2,n}\}$, more preferred $\{f_{1,1}, L_{1,1}\}=\{f_{1,n}, L_{1,n}\}$ and $\{f_{2,1}, L_{2,1}\}=\{f_{2,n}, L_{2,n}\}$.

In summary, the inventive achievement consists, among other things, in using an excitation scheme which is new compared to the state-of-the-art, preferably with (1) two different measurements according to PTA-II and PTA-I (with the choice of excitation frequencies and sound pressure level being subject to the above mentioned) or (2) one measurement according to PTA-II with extended $f_1$-pulse.

A decisive innovation is therefore, according to possibility (1), that for a given primary-tone pair the DPOAE response is compared with respect to two different excitation forms (PTA-I and PTA-II). This possibility is not provided for in the state-of-the-art. Stimulation by means of different forms of excitation can in principle influence the DPOAE response in three different ways:

Suppression: In the inner ear, the compressive non-linearity of the transmission curve of the mechanoelectric transduction, characterized by the limit states of completely open or closed ion channels, leads to the fact that the presentation of a second signal—i.e. here the switching on of the respective time-delayed primary tone—leads to so-called suppression effects; inevitably, because DPOAE are preferably generated when both primary tones arrive at the $f_2$-characteristic place simultaneously. In the inner ear, the travelling wave caused by a single primary tone is strongly dependent on an area that extends about ⅓ of an octave basally of its maximum. In this area, the outer hair cells of the travelling wave supply the additional energy in the correct phase, which leads to cochlear gain. Since both primary tones are chosen in such a way that they reach about the same amplitude at the $f_2$-characteristic place (i.e. the $f_1$-primary tone excites much more strongly since it continues to form its maximum apically), the $f_1$-primary tone with its flatter basal flank stimulates the outer hair cells in the region about ⅓ octave more strongly than the $f_2$-primary tone (which forms a relatively sharp maximum at the $f_2$-characteristic place). Therefore, the DPOAE responses differ depending on the excitation paradigm (PTA-I or PTA-II), because the outer hair cells lying basal to the $f_2$-characteristic place become more saturated in the case of initial excitation with the $f_1$-primary tone according to PTA-I and can no longer provide full amplification when generating the following $f_2$-primary tone.

DC shift: DC effects are the effects of a comparatively low-frequency, transient shift of the resting potential in the outer hair cells, and thus also of the position of the basilar membrane and the tectorial membrane. With normal physiological homeostasis in the inner ear, the working point is relatively close to the state of completely closed ion channels (i.e. clearly asymmetrical). At high amplitudes, where the input signal is clipped by both limit states, the low-pass filtered signal component (i.e. the transient resting potential shift) should merge into the middle potential. If the $f_1$-primary tone is switched on first according to PTA-I, this transition to middle potential took place in most cells before the $f_2$-primary tone is switched on and a DPOAE response could be measured. Therefore, the shift of the resting potential, which leads to a slight reduction in the gain provided by the outer hair cells, is not visible. In the PTA II arrangement, on the other hand, the $f_2$-primary tone arrives first, and in the area corresponding to ⅓ octave basal to the $f_2$-characteristic place, the full resting potential shift only takes place as soon as the $f_2$-primary tone is switched on. This resting potential shift therefore becomes visible when the DPOAE response first reaches a higher amplitude, but then decreases due to the resting potential shift. From this point on, the DPOAE responses of both excitation paradigms run almost identically until a similar effect can be observed when the system is switched off (removal of the shifted resting potential). This also explains the striking difference between the two DPOAE curves: In the PTA II excitation scheme, the DPOAE response rises approx. 2 ms earlier than in the PTA-I excitation scheme. This value corresponds to approx. ⅓ of the latency of the DPOAE responses for the frequency $f_2=2$ kHz (approx. 6 ms). The $f_1$-primary tone, which is switched on later, reaches the more basal $f_2$-characteristic place well before the DPOAE response reaches its maximum, and is not yet clearly band-limited at the $f_2$-characteristic place. Broadband signals generally lead to steeper edges in the time domain.

Efferent innervation of the outer hair cells. A sound creates a neural stimulus in the healthy ear that rises from the inner hair cells via the brainstem to the cortex. In the brainstem, interneurons couple the stimulus back to the outer hair cells via an efferent innervation, and lead to a slight attenuation of the cochlear amplifier in the healthy ear. However, this effect usually has a maximum attenuation of 1 dB as a consequence (<10% amplitude reduction); secondly, the time constant of this effect is about 40 ms, so according to current knowledge it cannot lead to the difference between the two pulse response forms.

If several pairs of primary tones (according to PTA-I or PTA-II) are presented in one measurement in the procedure according to the invention, the use of the pulse interlacing procedure described below may be appropriate in order to shorten the duration of the measurement. For this purpose, a set of the first primary-tone pair $\{f_{1,1}, L_{1,1}; f_{2,1}, L_{2,1}\}$ and the at least one further primary-tone pair $\{f_{1,n}, L_{1,n}; f_{1,n}, L_{2,n}\}$ is presented in a block which is repeated several times during the measurement period.

Advantageously, the inventive method may include a further step upstream to check at the beginning of the measurements whether the frequency $f_{dp}$ of one of the evoked DPOAEs interferes with a spontaneous emission (SOAE). This is particularly advantageous if several pairs of primary tones are to be presented during the measurement (e.g. according to the pulse interlacing method mentioned above). Artefacts and sources of interference can be detected at the beginning of the measurement. If this is the case, for example, the block time $T_B$ or the time duration $T_S$ can be adjusted for one or all slots so that the decay time of the DPOAE is extended to such an extent that its sound pressure level falls below a certain threshold before the next pair of primary tones is presented. Alternatively, the $f_2$-excitation frequency, for example, can be shifted to create a minimum distance to the SOAE.

Preferably for this purpose a DPOAE can be measured at the beginning of a measurement for a primary-tone pair with a first primary tone $\{f_1, L_1\}$ and a second primary tone $\{f_2, L_2\}$. If no DPOAE can be measured, the sound pressure levels $L_2$ and $L_1$ can be increased incrementally until either the maximum output sound pressure level $L_2$ or $L_1$ is reached or a DPOAE is measured. In this simple way, the presence of interfering SOAE can be detected and, if necessary, compensated.

Furthermore, the inventive method for determining individual level maps can be combined with the level map method described below.

For the effective suppression of the primary tones $\{f_1, L_1\}$ and $\{f_2, L_2\}$ the primary-tone-phase-variation method of Whitehead et al., 1996, loc. cit. is preferably used in addition to the usual filter methods. It is generally preferable to check at the beginning of the measurements whether the frequency of one of the DPOAEs ($f_{dp}$) interferes with a spontaneous emission (SOAE). The advantage here is that artefacts and sources of interference are already detected at the beginning of the measurement. If this is the case, the procedure can be adjusted to extend the decay time of the DPOAE to such an extent that its level falls below a certain threshold before the next pair of primary tones is presented, or to shift the frequency $f_2$ to establish a minimum distance to the SOAE.

The inventive methods can be used to determine the gain of the cochlear amplifier in a human or animal auditory organ and advantageously also to determine the cause of a possible loss of function. The procedures according to the invention are still suitable for the adjustment of a hearing aid.

FIGURES

Further advantages result from the following description of the attached figures.

FIG. 1 Comparison of the amplitudes of the envelopes of the $2f_1$-$f_2$-DPOAE after excitation by PTA-I (grey line) and PTA-II (black line).

Figure 2:
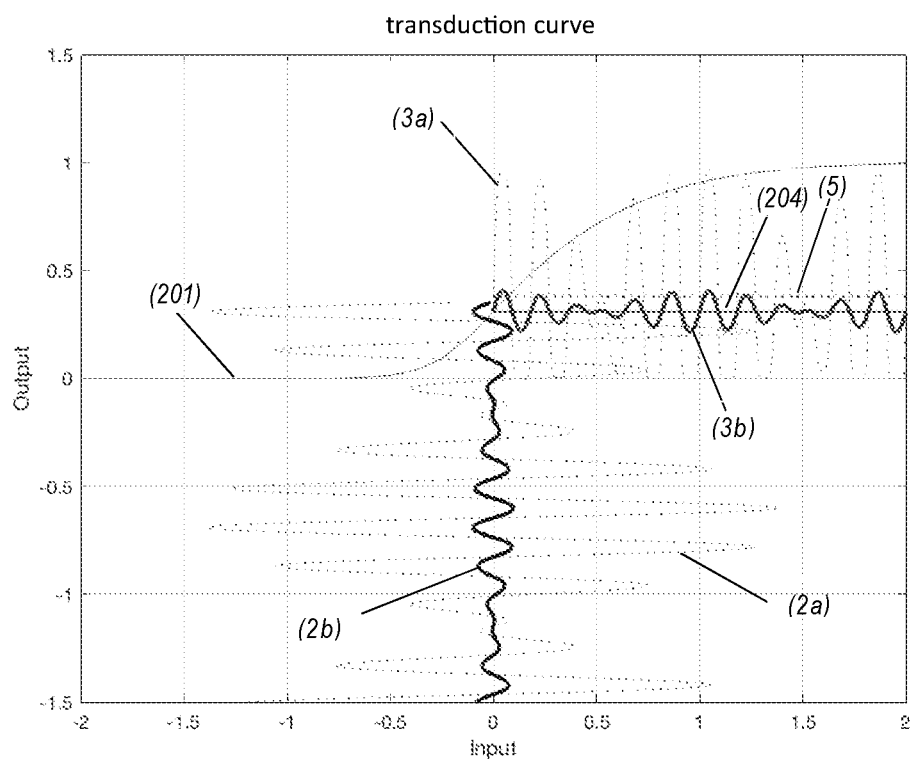

FIG. 2 Transduction curve of the OHC and its effect on the receptor potential for DPOAE excitation sounds of different strengths.

FIG. 3 Measurement of the SPDPOAE or the resting potential shift with an excitation with extended $f_1$-pulse (pulse length 20 ms).

Figure 4:
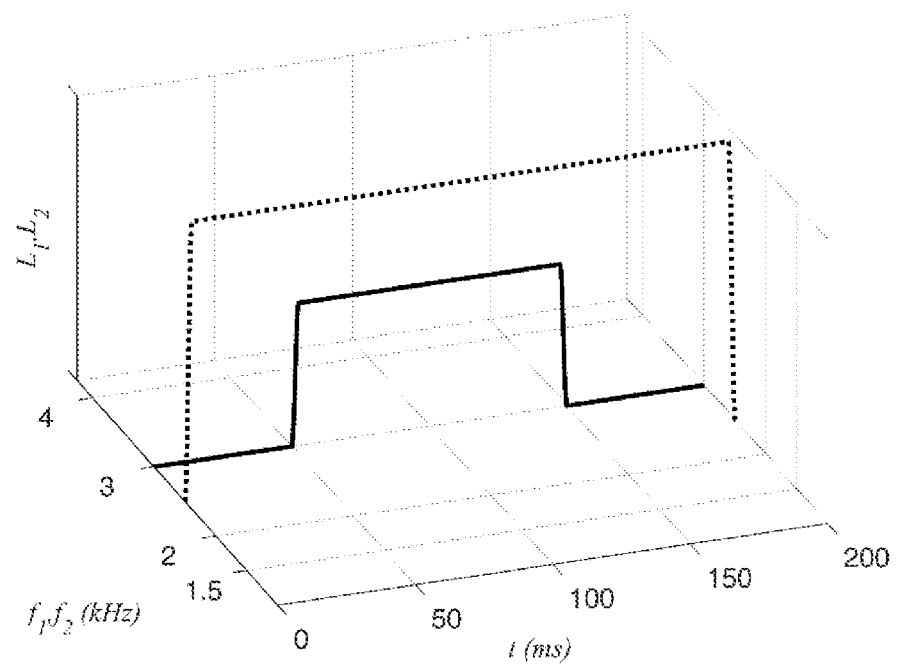

FIG. 4 State-of-the-art PTA-I excitation scheme in which the $f_2$-pulse (black, solid line) is presented during the continuous $f_1$-pulse (dotted line).

Figure 5:
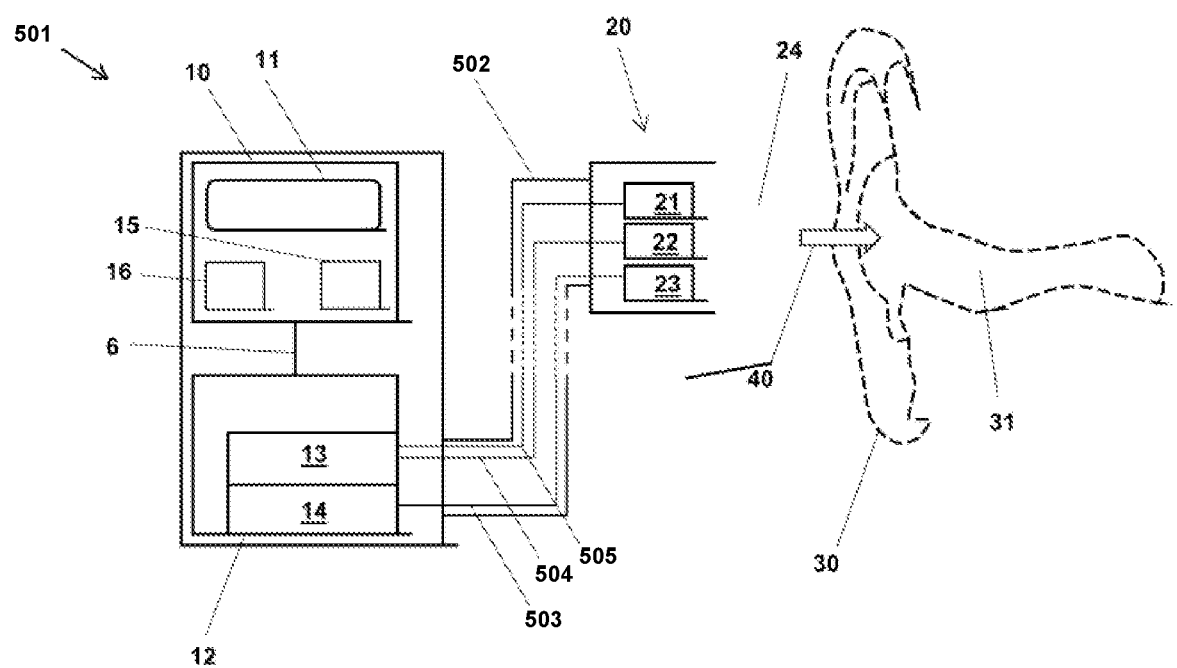

FIG. 5 A system for automatically determining an individual function of a DPOAE level map.

Figure 6:
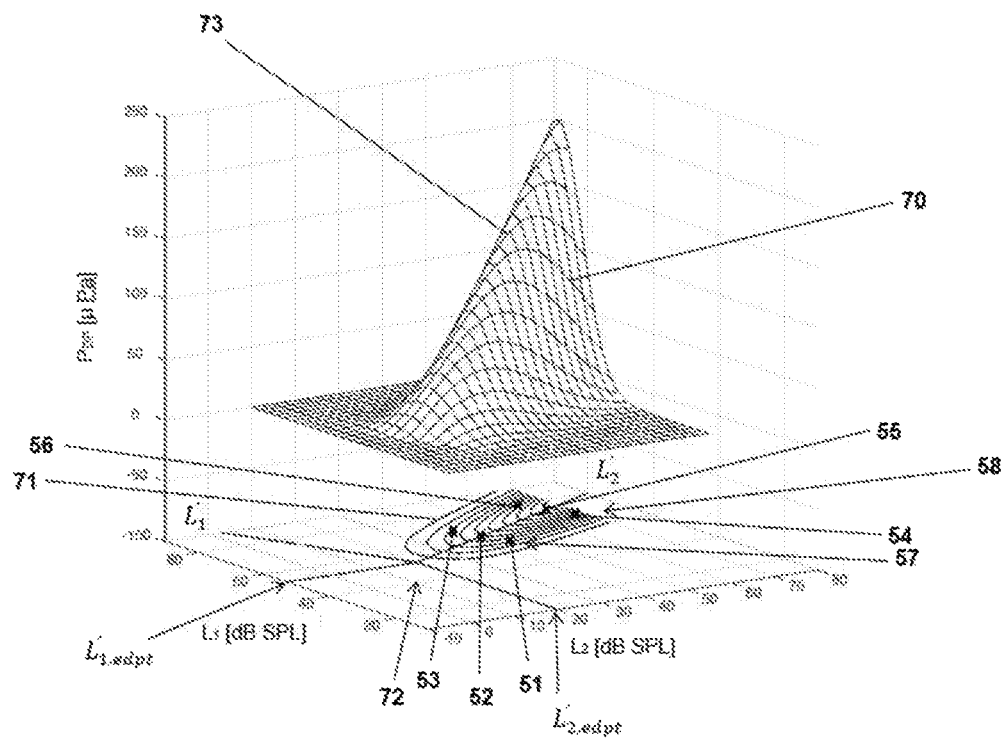

FIG. 6 A model function whose three-dimensional graph corresponds to a model level map.

Figure 7:
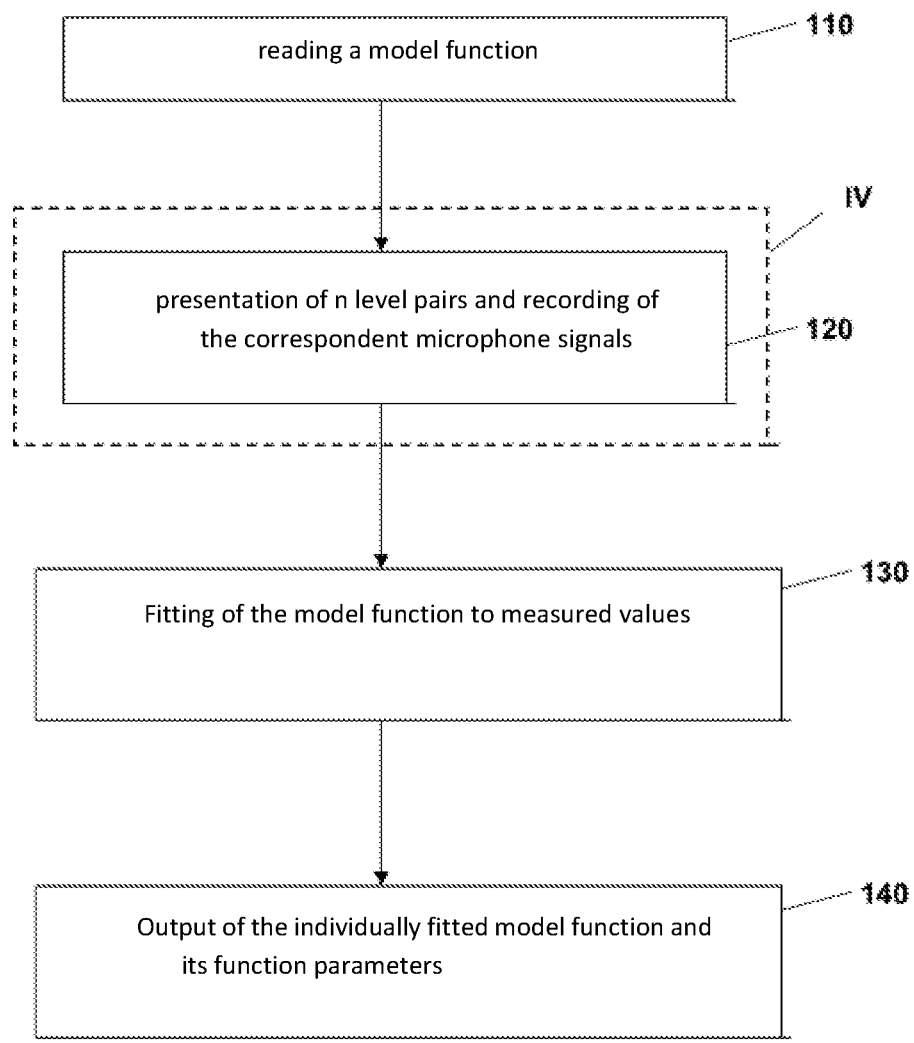

FIG. 7 Process steps for the automatic determination of an individual function of a DPOAE level map.

Figure 8:
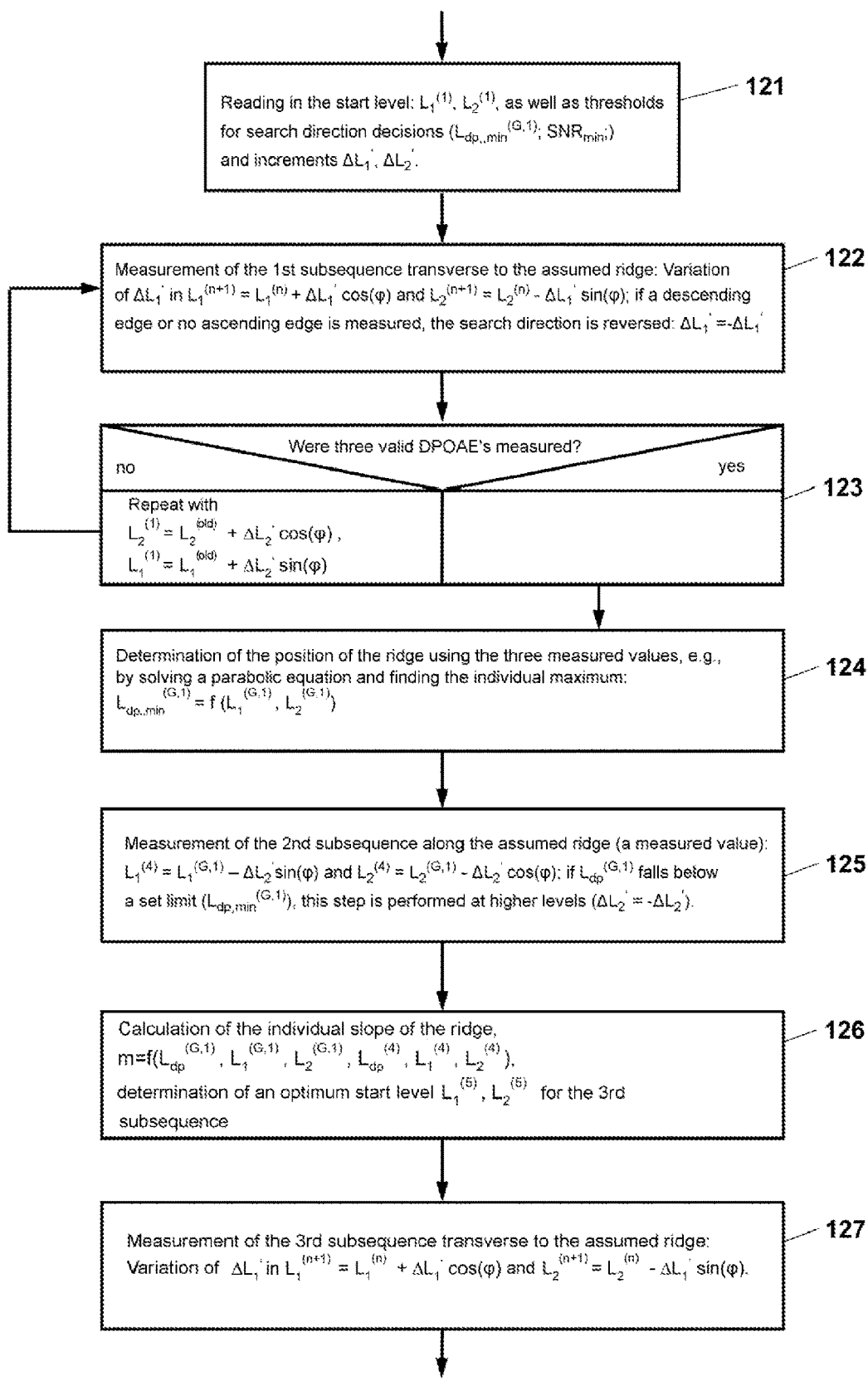

FIG. 8 Detailing of the procedural step according to the marking IV in FIG. 7.

Figure 9:
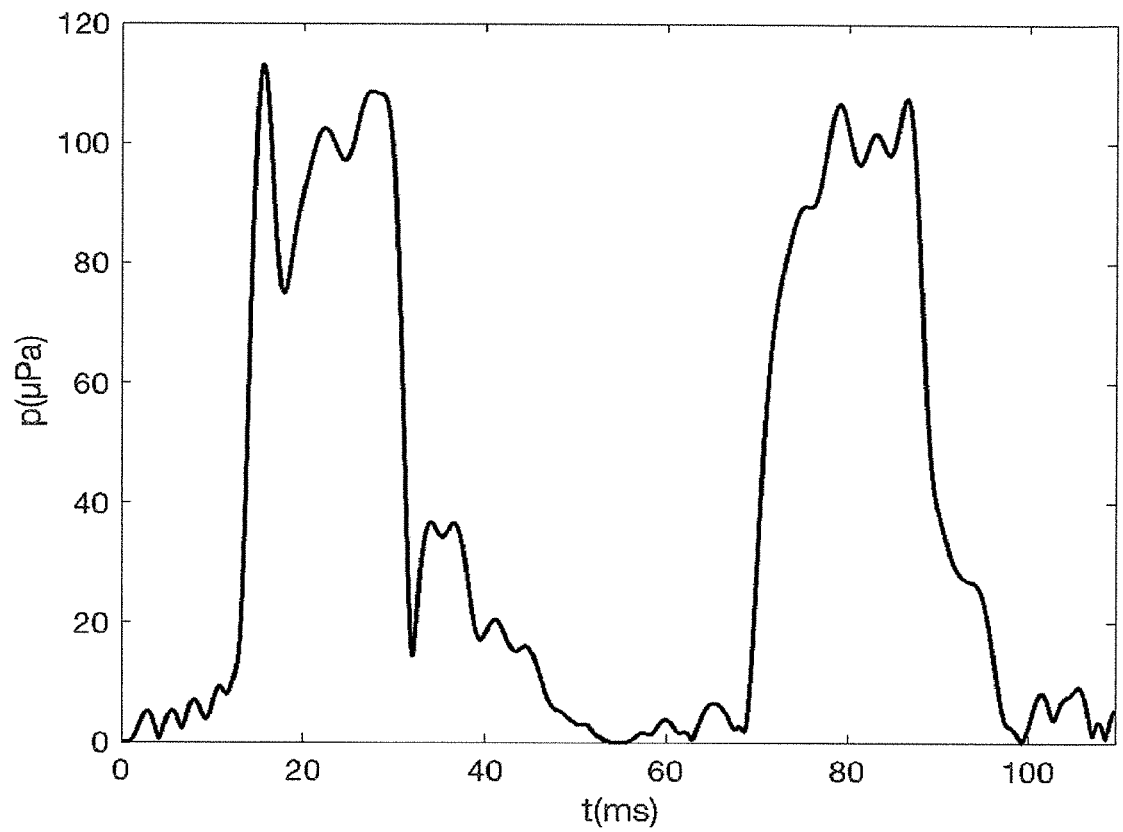

FIG. 9 Comparison of the amplitudes of the envelopes of the $2f_1$-$f_2$-DPOAE after excitation by PTA-II (left) and PTA-I (right).

Figure 10:
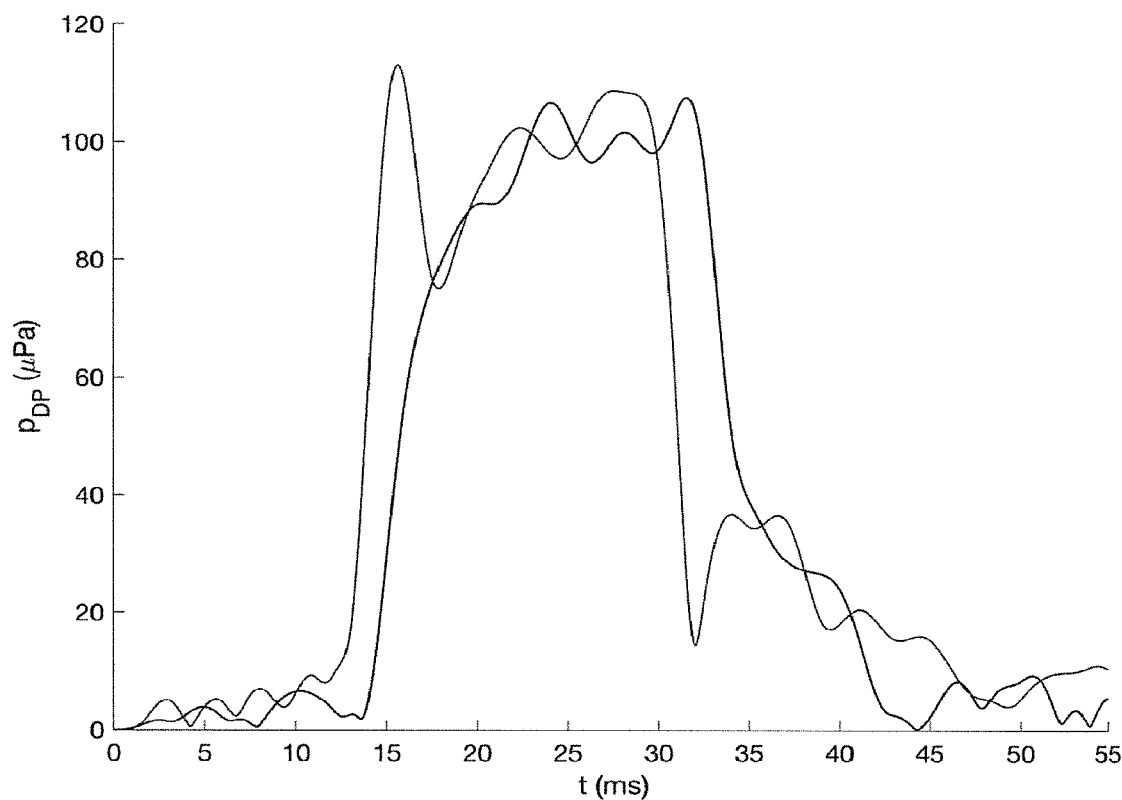

FIG. 10 Curves superimposed from FIG. 9.

It goes without saying that the features mentioned above and the features to be explained below can be used not only in the combination indicated, but also in other combinations or in a unique position, without leaving the scope of this invention.

Examples of how the invention may be executed are explained in more detail in the following description, with reference to the attached drawings.

FIG. 1 shows the envelopes of the $2f_1$-$f_2$-DPOAE after excitation by PTA-I (grey line) and PTA-II (black line). PTA-I and PTA-II lead to different amplitudes. If the $f_1$-tone is switched on later than the $f_2$-tone (here: 5 ms later) (PTA-II), a higher amplitude of the envelopes of the $2f_1$-$f_2$-DPOAE (black line) is obtained than if the $f_2$-tone is switched on 5 ms later than the $f_1$-tone (grey line) (PTA-I).

In this example, the response curves of the DPOAE show only the response of the nonlinear source, while the response of the coherent reflection source in this subject and at this frequency is too low to be detected. The response of the nonlinear source is relevant because its amplitude is normally greater and, unlike the coherent reflection source, it is not dependent on any additional process (roughness of the impedance function).

In this example, the response of the nonlinear source (i.e., the envelope of the $2f_1$-$f_2$-DPOAE time signal) is 3 dB greater for PTA-II than for PTA-I. This difference is large enough to be detected with certainty.

FIG. 2 shows the transduction curve of the OHC (201) and its effect on the receptor potential for DPOAE excitation sounds of different levels. Input is the deflection of the stereocilia, output is the receptor potential, which controls the force coupling of the cell into the vibrations of the organ and thus the amplification process. Since the ion channels can only be completely closed or completely opened, the transduction curve at high input values reaches a maximum or minimum value, in the normalization selected here the value 1 or 0. Furthermore, two input signals ((2a) and (2b)) are shown, which correspond to an excitation with two primary tones. The resulting beating signal is clearly visible. Firstly, it is excited with a relatively low amplitude ((2a), solid line), which responds to a still somewhat linear part of the transduction curve. Secondly, an excitation with a significantly higher amplitude is shown ((2b), dotted line), which is clearly processed non-linearly. The resulting output signals (3a, 3b) are also shown. In the case of small-signal excitation ((3a) solid, strong line), the system response cannot be visually distinguished from the input signal. (204) represents the mean value, i.e. the DC component of the signal. With stronger excitation (5) the influence of non-linearity is clearly visible. Due to the asymmetry of the transduction curve, the negative half-waves of the potential fluctuations are strongly cut off, while the positive half-waves still show a somewhat sinusoidal course. As a result, the mean value, i.e. the DC value of the potential fluctuations, shifts.

In a healthy case, the operating point shifts from the steepest point to a less steep one. This must lead to some reduction in the gain of the OHC. Preferably, the shift of the resting or DC potential takes place largely frequency-independently within 1-2 ms.

FIG. 3 shows the measurement of the SPDPOAE or the resting potential shift with an excitation with extended $f_1$ short pulse. If the second primary tone $\{f_2, L_2\}$ is switched on first and the extended $f_1$ short pulse delayed by 5 ms, in this example the DPOAE reaches a maximum of 113 µPa at the beginning, then drops by more than 3 dB within 2 ms, and then rises again. This subsequent increase can in principle be caused by the influence of the second source, but also by slower control processes of the difference between intra- and extracellular potentials. (301) Excitation by PTA-II, (302) Excitation by PTA-I.

Pulse Interlacing Method

The inventive method can also be combined with the pulse interlacing method known from WO 2015/192969 A1 ("time-limited multifrequency method").

Pulsed DPOAE have the disadvantage compared to continuous DPOAE that the measurement with one frequency sound-pressure level combination generally has a low duty factor and thus a correspondingly lower signal-to-noise ratio within the same measurement time. In the procedure described in WO 2015/192969 A1, however, this disadvantage is considerably reduced by interlacing several measurements in time-frequency space, i.e. presenting them alternately with a time delay. Within a block, for example, seven frequencies can be stimulated and analyzed with a time delay. The measurement procedure is thus accelerated by parallel and adaptive stimulation and analysis steps, and allows the measurement of growth functions for 5-7 frequencies $f_2$ in typically 2-2.5 min.

In the method described in WO 2015/192969 A1, at least two different pulse pairs (each with a pulsed first primary tone $\{f_1, L_1\}$) and a pulsed second primary tone $\{f_2, L_2\}$) with different excitation frequencies $f_2$ (and consequently different excitation frequencies $f_1$) are presented in a block which is repeated several times during a measurement period. In a block, a first primary tone pair presented in pulsed mode is followed by a first primary tone pair with $\{f_{2,1}, f_{1,1}\}$ a second pair of primary tones with different frequencies $\{f_{2,2}, f_{1,2}\}$ and if necessary further ones with $\{f_{2,n}, f_{1,n}\}$ wherein the frequency ratio is preferably always close to $f_{2,n}/f_{1,n}=1.2$ is held.

WO 2015/192969 A1 provides that the pulsed primary tones of each pair are presented according to the PTA-I excitation scheme (with $f_2$-short pulse). The $f_1$-pulse of a pair of pulses starts before the $f_2$-pulse and ends after the $f_2$-pulse has ended, i.e. the $f_1$-pulse is longer than the $f_2$-pulse of a pair of pulses.

The pulse interlacing method according to the invention provides for the presentation of at least one primary-tone pair according to the PTA-II excitation scheme (with $f_1$-short pulse). The other primary-tone pairs in a block can be presented either according to PTA-II (pure PTA-II pulse interlacing method) or according to PTA-I (combined PTA-I/PTA-II pulse interlacing method).

In the pulse interlacing method according to the invention, the beginning of a (PTA-I or PTA-II) pulse pair follows in a block, preferably with a time interval T ($T_{SLOT}$ or $T_S$), the beginning of the (PTA-I or PTA-II) pulse pair immediately preceding in the block, where $T_S$ generally corresponds at least to the length of the preceding pulse. Preferably $T_S$ is >10 ms. This measurement time reserved for a (PTA-I or PTA-II) pulse pair in a block is referred to below as the slot. It should be noted that slots do not overlap, but one slot follows the other when the previous slot is finished.

It is advantageous to present the second (PTA-I or PTA-II) pair of pulses in this way only after the DPOAE evoked by the first (PTA-I or PTA-II) pair of pulses has been sufficiently decayed (to approx. 1 to 10% of the output value) so that there are no noticeable interferences when measuring the sound pressure levels ($L_{dp}$) of the individual DPOAE, which have only a very low sound pressure level compared to the sound pressure levels $L_1$ and $L_2$ of the $f_1$ and $f_2$-pulses. In addition, the increased time interval between the presentation of (PTA-I or PTA-II) pulse pairs with the same excitation frequencies $f_1$ and $f_2$ allows sufficient recovery time for the complete decay of the DPOAE triggered in the previous measurement block.

Preferably, the or each block of (PTA-I or PTA-II) pulse pairs can be presented during a block time $T_B$. The block time $T_B$ is defined as the sum of the slot lengths $T_S$ of a block. Preferably, $T_B$ is chosen so that a (PTA-I or PTA-II) pulse has sufficiently approached its steady state when repeated. A time interval of 30 ms to 100 ms, preferably of at least 70 ms, preferably lies between the beginning of a first and a subsequent pulse pair with the same excitation frequency $f_2$.

Preferably, the $f_2$-excitation frequencies of two consecutive (PTA-I or PTA-II) pulse pairs in a block are at least one octave apart. The choice of such a frequency spacing of at least one octave between the $f_2$-excitation frequencies advantageously ensures that the frequencies $f_{dp}$ of the evoked DPOAE are sufficiently far apart so that there is preferably no noticeable interference when measuring the individual DPOAE.

For the excitation frequencies $f_1$ and $f_2$, the above-mentioned applies, for example a preferred frequency ratio of $f_1/f_2=1.2$. An example of two different pulse pairs of a block are a first pulse pair with an excitation frequency $f_2$ of 1.5 kHz and an excitation frequency $f_1$ of 1.25 kHz and a second pulse pair with an excitation frequency $f_2$ of 4 kHz and an excitation frequency $f_1$ of 3.33 kHz.

A preferred set (i.e. panel or frequency time pattern of excitation frequencies in a block.) of $f_2$ excitation frequencies in a block consists of the excitation frequencies $f_2=1$ kHz, $f_2=3$ kHz, $f_2=1.5$ kHz, $f_2=6$ kHz. These $f_2$-excitation frequencies are repeatedly presented in a block in this order. Another preferred set (panel) of $f_2$-excitation frequencies in a block consists of the excitation frequencies $f_2=2$ kHz, $f_2=4$ kHz, $f_2=1.5$ kHz, $f_2=3$ kHz.

Depending on the frequency, the (PTA-I) $f_1$-pulse can preferably be switched on 3-10 ms earlier and switched off 3-10 ms later than the (PTA-I) $f_2$-pulse, so that the (PTA-I) $f_1$-pulse briefly reaches a steady state during the presentation of the (PTA-I) $f_2$-pulse.

However, it is also possible to work with two equally or similarly short (PTA-I) $f_1$ and $f_2$-pulses, which are so time-shifted that both excitations occur simultaneously at the diagnostically most valuable characteristic place of the (PTA-I) $f_2$-pulse in the cochlea, in order to save as much time as possible. Then the (PTA-I) $f_1$-pulse is switched on about 0.1-3 ms later, since its propagation time to the more basal (direction of the foot plate) place of the $f_2$-pulse is shorter than for the (PTA-I) $f_2$-pulse. If this setting is selected optimally, there is no effect from the afferent-efferent feedback loop of the medial olivocochlear reflex.

The duration (length) of the (PTA-I) $f_1$ and $f_2$-pulse in a pulse pair can preferably be 2 to 20 ms. With regard to the pulse length, the above applies with regard to PTA-II.

In the pulse interlacing procedure of the present invention, the sequence of the pulse pairs and the time interval between two successive (PTA-I and/or PTA-II) pulse pairs, i.e. the slot time ($T_{SLOT}$), can be constant in a block. With this block rigid procedure, as many blocks are measured and averaged until the desired SNR is reached for each excitation frequency in the set (panel). Alternatively, if the desired SNR for one excitation frequency $f_2$ is reached, the remaining pulse pairs for this excitation frequency $f_2$ and consequently their averages can be skipped. In addition, the remaining pulse pairs can be used to continue measuring in shortened blocks, i.e. with fewer slots, which further shortens the measuring time.

Furthermore, two sets with at least partially different (PTA-I and/or PTA-II) pulse pairs with respect to the second excitation frequency $f_2$ can be selected in the pulse interlacing method of the present invention according to the invention, wherein the blocks of the individual sets are presented one after the other in time and the DPOAE are measured and averaged. The blocks are therefore processed one after the other. In this block-flexible method with fixed pulse arrangement, for example, seven (PTA-I and/or PTA-II) pulse pairs with different excitation frequencies $f_2$ are arranged in such a way that, according to general experience, they are all assigned approximately the averaging time required to achieve a certain signal-to-noise ratio.

Preferably, according to the invention, several sets are presented one after the other, to which (PTA-I and/or PTA-II) pulse pairs are distributed in such a way that (PTA-I and/or PTA-II) pulse pairs with low excitation frequencies $f_2$ (and thus also low excitation frequencies $f_1$) occur in several sets.

Using the pulse interlacing method according to the invention, it is also possible to continuously check for each (PTA-I and/or PTA-II) pulse pair whether a desired SNR is achieved. For the further measurement the (PTA-I and/or PTA-II) pulse pairs can be discarded for this excitation frequency $f_2$ and the remaining (PTA-I and/or PTA-II) pulse pairs can be redistributed to the blocks if necessary.

In this block-flexible method with free (PTA-I and/or PTA-II) pulse pair arrangement, the length of the measurements for the individual (PTA-I and/or PTA-II) pulse pairs is no longer fixed relative to each other. Instead, for each (PTA-I and/or PTA-II) pulse pair, the SNR is continuously checked to see if it has been reached; as soon as this is the case, the SNR is checked to see if another (PTA-I and/or PTA-II) pulse-pair measurement is incomplete. In this way, the completed (PTA-I and/or PTA-II) pulse-pair measurements are successively eliminated from the measurement, and only the remaining (PTA-I and/or PTA-II) pulse pairs are further presented. On the one hand, it is checked whether the octave spacing between two consecutive (PTA-I and/or PTA-II) pulse pairs is maintained. If this is no longer the case, (PTA-I/PTA-II) pulse pairs may no longer be processed in the blocks to which they were originally assigned, but in other (newly defined) blocks. In addition, it is checked whether the required time interval T (corresponding to the time for a slot ($T_{SLOT}$) plus the required decay time ($T_{decay}$)) between (PTA-I and/or PTA-II) pulse pairs with the same excitation frequency $f_2$ is observed.

As described above with regard to PTA-II, the sound pressure levels of the (PTA-I and/or PTA-II) pulse pairs within a block are preferably similar.

The DPOAE is preferably measured and averaged for all excitation frequencies $f_2$ contained in the set or sets at a sound pressure level $L_2$ assigned in each case to the excitation frequency, and then at least one new measurement is carried out at new sound pressure levels $L_2$, the new sound pressure level $L_2$ for the respective new measurement being determined preferably in a threshold value approximation method from the measured DPOAE for each excitation frequency $f_2$. This procedure is repeated until for each excitation frequency $f_2$ a growth curve can be determined from measured values of the sound pressure levels of the DPOAE for 3 to 4 different sound pressure levels $L_2$, from which the respective threshold values are then determined. A more detailed description of this procedure can be found in WO 2015/192969 A1.

Level Map Method

The procedure according to the invention can be combined with the level map method known from PCT/EP2017/000334. A "DPOAE level map" (DPOAE level map, see Shera and Guinan, J Acoust Soc Am. 2007 February; 121 (2):1003-16) and Martin et al. J. Acoust. Soc. Am. 127 5, p. 2955-2972) denotes the amplitude of a level (here the $2f_1$-$f_2$ distortion product) as a function of the primary tone levels.

The procedure described in PCT/EP/2017/000334 is used to automatically determine an individual function of a DPOAE level map. This is preferably done to avoid errors in the extrapolation of growth functions, which may occur in other state-of-the-art methods for measuring the distortion product threshold $L_{edpt}$ due to their principle. The procedure described in PCT/EP2017/000334 can be used for conventional (i.e. quasi continuous) measured (PTA-II excited) DPOAE. It can also be combined with a pulsed (PTA-II excited) DPOAE process as described in DE 102014108663 A1. In particular, the procedure described in PCT/EP2017/000334 can be combined with the combined pulse interlacing described above.

In particular, the procedures of the present invention can include the following steps for automatically determining an individual function of a DPOAE level chart with $p_{dp,I}=f(L_1, L_2)$ of a human or animal hearing:

Reading a model function $p_{dp,M}=f(L_1, L_2)$ with model parameters of a DPOAE level map based on a number of N DPOAE measurements of an excitation frequency pair $\{f_1, f_2\}$ each with different level pairs $\{L_1^{(1 \cdots N)}, L_2^{(1 \cdots N)}\}$ in a population (p) of normal hearing persons into a main memory of a computer unit, where N is $\geq 40$ and $p \geq 2$, automatic presentation of n different level pairs $\{L_1^{(1 \cdots N)}, L_2^{(1 \cdots N)}\}$ of an excitation frequency pair $\{f_1, f_2\}$ via sound output means to an individual and detecting the corresponding DPOAE of the individual via sound recording means, wherein at least the first level pair $\{L_1^{(1)}, L_2^{(1)}\}$ is predefined and where n is $\ll N$, iterative adjustment of the model function $p_{dp,M}=f(L_1, L_2)$ to the measured n DPOAE until an individual function is obtained $p_{dp,I}=f(L_1, L_2)$ with individual parameters of a DPOAE level chart of the individual by the computer unit, and Output of the individual function $p_{dp,I}=f(L_1, L_2)$ and/or their individual parameters at an output unit of the computer unit.

With iterative fitting (curve fitting), the model function is fitted to experimentally determined measured values. For this purpose, parameters of this function are changed with a suitable algorithm until the deviation between the measured values and the stepwise changed function according to an optimality criterion is minimal (e.g. minimization of the quadratic error). Algorithms for such an iterative adaptation are known to the expert from the state-of-the-art (e.g. Isqcurvefit or Isqnonlin).

The first level pair $\{L_1^{(1)}, L_2^{(1)}\}$ can set a level $L_1$ of $67 \pm 10$ dB and a level of $L_2$ of $57 \pm 10$ dB. These levels of $L_1$ and from $L_2$ have proven to be particularly favourable initial levels. For normal hearing people, these excitation levels are still in the range up to which the level map increases approximately linearly, and even with hearing losses of up to approx. 40 dB, a DPOAE can still be measured at these levels. Thus, in most cases, values are obtained that are valid for the recording of the level map.

The model function defines a linearly rising ridge, to which $\{L_1^{(G)}, L_2^{(G)}\}$ level pairs are assigned with linearly interrelation (where "G" is the index for "assigned to the ridge"). Preferably, at least half of the measured level pairs $\{L_1^{(i)}, L_2^{(i)}\}$ can be positioned by at least 5 dB to both sides off the ridge assigned to the $\{L_1^{(G)}, L_2^{(G)}\}$ level pairs (where "i" is the index of the measurement from 1 to n).

The different level pairs $\{L_1^{(i)}, L_2^{(i)}\}$ are preferably presented in a sequence that is identical for each individual. This greatly simplified and standardized (rigid) procedure makes the approximation to the individual function of a level map somewhat less accurate, but this procedure is very fast in execution.

It can also be advantageous if the pre-defined, different level pairs ($L_1$, $L_2$) are presented in a sequence comprising a number of k subsequences whose level pairs are $\{L_1, L_2\}$ substantially transverse to the level pairs linearly linked to each other and associated with the ridge $\{L_1^{(G)}, L_2^{(G)}\}$ lie. By switching on the subsequences, the ridge can be scanned in several places, which increases the accuracy of determining the individual function of the DPOAE level chart.

Preferably, n≥5 and ≤12, preferably 6≤n≤8. Due to the small number of planned measurements, a short measurement duration is achieved while the individual function of the DPOAE level map is recorded with high quality.

The number of subsequences k≥2 and ≤5 is advantageous, whereby a good sampling of the ridge of the DPOAE level map is achieved.

It is also advantageous if the level pairs $\{L_1^{(2 \cdots n_i)}, L_2^{(2 \cdots n_k)}\}$ of the subsequence with $n_k$ measurements following the first predefined level pair $\{L_1^{(1)}, L_2^{(1)}\}$ are determined via a function $\{L_1^{(i)}, L_2^{(i)}\} = \{L_1^{(i-1)} + \mu \cdot \Delta L_1, L_2^{(i-1)} + \mu \cdot \Delta L_2\}$ from the respective previous level pair $L_1^{(i-1)}$, $L_2^{(i-1)}$, where $\mu = \pm 1$, in particular +1, and $\Delta L_1$, $\Delta L_2$ denotes a level distance of two successive level pairs and values of $\Delta L_1 = 4$ to 14 dB, preferably from 6 to 10 dB, and $\Delta L_2 = 0$ up to $-2.78$ dB, preferably $\Delta L_2 = -1.52$ to $-2.78$ dB. The factor $\mu$ defines the search direction (towards smaller or larger $L_1$ measurement levels) across the ridge.

Preferably, if the first pair of levels is $\{L_1^{(1)}, l_2^{(1)}\}$ and the second pair of levels $\{L_1^{(2)}, L_2^{(2)}\}$ generates two DPOAE with $p_{dp,I}^{(1 \cdots 2)}$ which each have a signal-to-noise ratio of $>=4$ dB, preferably $>=10$ dB, the level of a subsequent third pair of levels $\{L_1^{(3)}, L_2^{(3)}\}$ is set at least by $\Delta L_1 \geq 4$ dB differently than the level of the previous level pair $\{L_1^{(2)}, L_2^{(2)}\}$ if $p_{dp,I}^{(2)} - p_{dp,I}^{(1)} > 0$, and, on the other hand, the level of a subsequent pair of levels $\{L_1^{(3)}, L_2^{(3)}\}$ at least by $\Delta L_1 \leq -4$ dB set differently than the level of the first level pair $\{L_1^{(1)}, L_2^{(1)}\}$ if $p_{dp,I}^{(2)} - p_{dp,I}^{(1)} \leq 0$. This procedure ensures that at least one point is measured to the left and one point to the right of the ridge and, in between, a point near the ridge.

Preferably, if the first pair of levels $\{L_1^{(1)}, L_2^{(1)}\}$ generates no DPOAE $p_{dp,I}^{(1)}$ which have a signal-to-noise ratio of $>=4$ dB, preferably $>=10$ dB, the search is continued in the same direction until either the maximum or minimum excitation level $L_1^{(i)}$ or a group of three valid DPOAE with $p_{dp,I}^{(i \cdots i+2)}$ which each have a signal-to-noise ratio of $>=4$ dB, preferably $>=10$ dB. In contrast to a rigid procedure, this ensures that the ridge is also found if it is positioned clearly apart from the position to be expected for normal hearing, as may be the case with sound-conduction loss, for example.

Preferably, if in the first subsequence after measurement at i excitation level pairs no group of three valid DPOAE is produced which each have a signal-to-noise ratio of $>=4$ dB, preferably $>=10$ dB, a further subsequence with a higher level pair $\{L_1^{(i+1)}, L_2^{(i+1)}\}$ is started, whereby the start level pair for the new subsequence is set to $L_2^{(i+3)} = L_2^{(1)} + 20 \pm 10$ dB, $L_1^{(i+3)} = L_1^{(1)} + 20 \pm 10$ dB is set. The level is preferably limited to the maximum technically achievable or reasonable level. This maximum level can be e.g. 75-85 dB SPL sound pressure. By this procedure, individual level maps and/or their function can still be determined, even if they are strongly deviating from the average.

Preferably, after the acquisition of the DPOAE of at least 3 level pairs $\{L_1^{(1 \cdots 3)}, L_2^{(1 \cdots 3)}\}$ which are preferably belonging to a subsequence, from these 3 level pairs $\{L_1^{(1 \cdots 3)}, L_2^{(1 \cdots 3)}\}$ the position of the ridge $\{L_1^{(G)}, L_2^{(G)}\}$ is determined along the line formed by the 3 level pairs, and then a fourth level pair $\{L_1^{(4)}, L_2^{(4)}\}$ is acquired lying at a given distance downhill near the ridge, where the group mean of the ridge direction, $\varphi$ is used to estimate its position and wherein, on the basis of the level pairs presented from the four $\{L_1^{(1 \cdots 4)}, L_2^{(1 \cdots 4)}\}$ a gradient m of the linear ridge of the level map is determined for a certain DPOAE.

Preferably, if in the first or second subsequence a group of three valid DPOAE is recorded with $p_{dp,I}^{(i-2 \cdots i)}$ having a signal-to-noise ratio of $>=4$ dB each, preferably $>=10$ dB, by automatically adapting a suitable calculation function to the corresponding DPOAE $p_{dp,I}^{(i \cdots i-2)}$ the level pair below the ridge $\{L_1^{(G)}, L_2^{(G)}\} = \{L_1^{(i-2)} + \varepsilon \cdot \Delta L_1, L_2^{(i-2)} + \varepsilon \cdot \Delta L_2\}$ is determined where $\varepsilon$ is calculated so that $p_{dp,I}(L_1^{(G)}, L_2^{(G)})$ forms a maximum, and from there a fourth pair of levels $\{L_1^{(i+1)}, L_2^{(i+1)}\}$ is presented, with a function $\{L_1^{(i+1)}, L_2^{(i+1)}\} = \{L_1^{(i)} + \Delta L_1, L_2^{(i)} + \Delta L_2\}$ where $\Delta L_2 = -15 \pm 10$ dB, and the level pair is preferably set on the projection of the expected ridge on the $L_1$, $L_2$-plane, i.e. with $\Delta L_1 / \Delta L_2 \approx 0.51 \pm 0.15$ and where, based on the level pairs presented from the four $L_1^{(i-2 \cdots i+1)}, L_2^{(i-2 \cdots i+1)}$ the slope m of the approximately linear ridge of the level map is determined.

On the basis of the determined slope m of the linear ridge of the level map, at least two, preferably three, further level pairs $L_1^{(i+1 \cdots i+3)}, L_2^{(i+1 \cdots i+3)}$ are automatically defined, whose excitation levels are grouped in a subsequence, and which are determined on the basis of the already known position and slope of the ridge in such a way that valid DPOAE can be expected within a measurement time of $t_m \leq 40$ s by adapting a model function to the four preferably already valid measured DPOAE, and then determining the last two or three pairs of levels in the model function in such a way that the expected DPOAE levels are preferably measured at $p_{DP,I}^{(i+1 \cdots i+3)}, p_{DP,I}^{(i+1 \cdots i+3)} \geq 10$ µPa.

Preferably the level pairs $\{L_1^{(1-n)}, L_2^{(1-n)}\}$ are presented pulsed with a duration $T_D$ of 2 to 40 ms. By using such a pulsed presentation, the influence of the two source contributions of a DPOAE can be suppressed or separated.

Preferably, the level pairs $\{L_1^{(1 \cdots n)}, L_2^{(1 \cdots n)}\}$ are presented in blocks of several subsequent pulsed level pairs $\{L_1^{(1 \cdots n)}, L_2^{(1 \cdots n)}\}$, where level pairs $\{L_1^{(1 \cdots n)}, L_2^{(1 \cdots m)}\}$ following directly each other are presented with different excitation frequencies $\{f_2, f_1\}$. In one block, a first pulsed level pair with $\{f_{2,1}, f_{1,1}\}$ is followed by a second pair of levels with different frequencies $\{f_{2,2}, f_{1,2}\}$ and if necessary further ones with $\{f_{2,m}, f_{1,m}\}$, wherein the frequency ratio is always close to $f_{2,m}/f_{1,m} = 1.2$. Several blocks with time-frequency interlaced pulse pairs can be averaged before evaluation takes place. This measure makes it possible to use the time in which the pulse response to a presentation decays at one frequency pair to measure at another frequency, thus reducing the measurement time compared to a purely sequential approach with regard to the desired measurement frequencies.

The individual function of a DPOAE level map and its parameters determined by the computer unit are stored in a non-volatile memory in one processing step. The raw data determined by the computer unit can also be stored in the non-volatile memory. The stored data can be used by the computer unit for the continuous extension of the data set underlying the model function of a level map.

FIG. 5 shows a system for the automatic determination of an individual function of a DPOAE level map of a human or animal hearing in a possible configuration. System 501 includes a probe unit 20 that can be positioned on one ear, in particular an OAE probe, and a computer unit 10. The probe unit has a probe tip 24 that can be inserted into the ear canal of one ear. The probe unit 20 contains a sound recording device 23, e.g. a microphone, which is set up to record sounds coming from the auditory canal. In the probe unit 20 a first and a second sound output means 21 and 22 are further provided which function as $f_1$ sound emitters (sound output means 21) and as $f_2$-sound emitters (sound output means 22). The sound output devices 21, 22 can be designed as loudspeakers, for example. It is also possible to provide only one sound output medium or only one loudspeaker, which is set up for simultaneous playback of two tones $f_1$, $f_2$ and in particular has a highly linear characteristic. The probe unit 20 is, for example, connected via a cable connection 502 to the control unit, which contains the computer unit 10. Cable connection 2 preferably contains shielded cables 503, 504, 505 via which the sound output devices 21, 22 and the sound recording device 23 are connected to an AD/DA converter unit 12 of the control unit. The AD/DA converter unit 12 is in turn connected to the computer unit 10 via at least one line 6 for bi-directional data exchange. As an alternative to cable connection 2, the probe unit 20 could also communicate wirelessly with the control unit or with the computer unit 10. The wireless connection could be, for example, a Bluetooth® radio link or another suitable radio connection that preferably has a short range.

The computer unit 10 has a working memory of 15 and a non-volatile memory of 16 in which a model function $p_{dp,M}=f(L_1, L_2)$ for a model level map of a human or animal auditory system and the parameters associated with that model function. The non-volatile memory 16 also contains the instructions for carrying out a procedure described here. System 1 also has an output device 11 or a display unit, such as a display, monitor or the like, through which a determined individual function of a DPOAE level map of a human or animal hearing and its parameters can be output by System 1 and made accessible to a user. The output device 11 can also be implemented in the form of an interface via which an external output device, such as a printer or monitor, can be connected to the system.

To perform an automatic measurement operation to create an individual function of a DPOAE level map of a human or animal ear, the probe unit 23 is inserted into the ear canal 31 of an ear 30 (indicated in FIG. 5) in the direction of arrow 40. The procedure is explained below with reference to FIGS. 7 and 8.

First, however, FIG. 6 shows an example of a model function whose three-dimensional graph 70 corresponds to a model level map. The model function presented as an example is based on the measured data from p≥2, available p=6, normal hearing individuals with N≥40, available N=47, measured different level pairs $\{L_1^{(1 \cdots N)}, L_2^{(1 \cdots N)}\}$ at excitation frequencies $f_2=2$ kHz and $f_1=1.67$ kHz. The excitation frequencies $f_2$ and $f_1$ of a level pair $\{L_1, L_2\}$ are preferably linked via a frequency ratio $f_2/f_1=1.2$. A certain distortion product was evaluated, which preferably lies at the frequency $f_{dp}=2f_1-f_2$. The superscript indices in brackets indicate the 1st to N-th measuring point.

The model function defines an approximately linearly increasing ridge 73, which is linked to approximately linearly related level pairs $\{L_1^{(G)}, L_2^{(G)}\}$. Lines across the ridge can be defined by the relationship $L_2+aL_1=C$ where C is any constant, and where a is the slope parameter of the projection of the ridge onto the $\{L_1, L_2\}$-plane. In a mathematical sense, the position of the ridge is defined by a series of gradient vectors of the scalar field formed by the DPOAE, with all other field lines formed by gradient vectors running towards this ridge and swiveling in. Into the $\{L_1, L_2\}$-plane 71 depicted below and being shifted by $p_{dp}=100$ μPa for the sake of clarity, the transformed $\{L_1', L_2'\}$-coordinate system 72 as well as contour lines of the level map at 20 μPa intervals are drawn. The coordinate system 72 is generated by shifting the origin to the $\{L_{1,edpt}, L_{2,edpt}\}$ and by rotation by arc tan (a). The $L_2'$-axis corresponds to the projection of the ridge of the level map on the $\{L_1, L_2\}$-plane. The $L_1'$-axis orthogonally cuts the model hill fitted to the level map. This section through the hill transverse to the ridge is approximated by a 2-nd order parabola, the spread of which is given by a parameter c, and which enters the following equation:

$$L_{dp}' = -c(L_1')^2 + L_{dp}'^{(G)}$$

with $$L_{dp}'^{(G)} = 30 \log_{10}(m(L_2'))$$

$L_{dp}'$ and $L_{dp}'^{(G)}$ is the level of any DPOAE or a DPOAE on the ridge and m is the slope of the ridge along the $L_2'$-axis.

The $\{L_1', L_2'\}$-coordinate system is located in the coordinate system defined by the known coordinate system $\{L_1, L_2\}$ of the primary tone level. The previously mentioned coordinate transformation can be expressed as follows:

$$L_1' = (L_1 - L_{1,edpt})\cos(\varphi) - (L_2 - L_{2,ept})\sin(\varphi)$$

$$L_2' = (L_1 - L_{1,edpt})\sin(\varphi) + (L_2 - L_{2,ept})\cos(\varphi)$$

Here, the projection of the ridge of the $L_{dp}$-hill onto the $\{L_1, L_2\}$-plane corresponds to the $L_2'$-axis. Furthermore, at the point $\{L_{2,edpt}, L_{1,edpt}\}$ the ridge of the $L_{dp}$-hill intersects the $\{L_1, L_2\}$-plane, and φ is the angle between the $L_2$-axis and the projection of the ridge of the $L_{dp}$-hill onto the $\{L_1, L_2\}$-plane, given by the already mentioned $L_2'$-axis. The angle φ is therefore the angle by which the $L_2'$-axis is rotated with respect to the $L_2$-axis. The base of the ridge can be interpreted in a broader sense as equivalent but not identical to the estimated distorsion product level (edpt) as known from [P. Boege and T. Janssen., *J. Acoust. Soc. Am.,* 111(4): 1810-1818, 2002].

For positive $L_{dp}$ values, the model function for the level map is valid and can be described by five free parameters: a; b; c; $L_{2,edpt}$; m. To be able to calculate this function from measured values, at least 5 DPOAE are required.

The method is based on the adaptation of the three-dimensional model function to a coarsely sampled three-dimensional DPOAE level map with preferably at least 5 measurements. In a first execution example of the procedure for the automatic determination of an individual function of a DPOAE level map with $p_{dp}=f(L_1, L_2)$ of a human or animal hearing, the ear of an individual is presented with n predefined, e.g. n=6 predefined, excitation level pairs from the system shown in FIG. 5 $\{L_1, L_2\}$ 51, 52, 53, 54, 55, 56.

These six predefined excitation level pairs $\{L_1, L_2\}$ 51, 52, 53, 54, 55, 56 are shown as examples in FIG. 6 of the $\{L_1, L_2\}$-level being selected. From these 6 predefined excitation level pairs $\{L_1, L_2\}$ 51, 52, 53, 54, 55, 56, presented in two subsequences 57, 58, DPOAE are then determined, which are used via the procedure for determining the individual function of a DPOAE level map.

According to FIG. 7, in a first step 110 of the procedure, the model function already described is first read from the non-volatile memory 16 into the computer unit 10 of system 1 or the working memory 15 of the computer unit 10. After the model function has been read in, system 1 in the second step 120 generates a number of different level pairs. $\{L_1^{(1 \cdots n)}, L_2^{(1 \cdots n)}\}$, of an excitation frequency pair $\{f_1, f_2\}$ is output or presented to an individual via the sound output means 21, 22 of the probe unit 20 and the corresponding DPOAE of the individual is detected via the sound recording means 23, wherein at least the first pair of levels $\{L_1^{(1)}, L_2^{(1)}\}$ is predefined and where n is <<N. The corresponding DPOAE are sent by the AD/DA converter unit 12 to the computer unit 10 for further processing. The superscripts in brackets indicate the 1st to n-th measuring points.

The second step 120 contains a series of substeps 121 to 127 in a first variant of the procedure, which can be described as an adaptive variant, which are explained in more detail below with reference to FIG. 8.

According to FIG. 8, in a first substep 121 of the second step 120, first a start level $\{L_1^{(1)}, L_2^{(1)}\}$ (preferably a level of $L_1$ of 67±10 dB and a level of $L_2$ of 57±10 dB) for a first level pair is read from the non-volatile memory 16 into the computer unit 10. Furthermore, in this substep 121, the step sizes $\Delta L_1$, $\Delta L_2$ for the other level pairs $\{L_1^{(2 \cdots n)}, L_2^{(2 \cdots n)}\}$ as well as thresholds for search direction decisions $L_{dp,min}^{(G, 1)}$ SNRmin) are read into the computer unit 10. SNRmin denotes the desired SNR (signal-to-noise ratio) and $L_{dp,min}^{(G, 1)}$ denotes the DPOAE level on the ridge, which must be present at least along a first subsequence of k subsequences, so that a next subsequence below the first can still be expected with sufficient SNR. If this value is not reached, the next subsequence is sampled above the first, i.e. up hill, in order to avoid too long a measurement time to reach a sufficient SNR. The step sizes $\Delta L_1$, $\Delta L_2$ denote the level spacing of two successive level pairs where $\Delta L_1$ in particular has a value of $\Delta L_1$=4 to 14 dB, preferably from 6 to 10 dB, and wherein $\Delta L_2$=0 is up to −2.78 dB, preferably $\Delta L_2$=−1.52 to −2.78 dB.

In a second substep 122 of the second step, the measurements of the first subsequence of k subsequences are now performed across the assumed degree of individual function of a level map. The DPOAE are performed at the excitation frequencies $f_2$=2 kHz and $f_1$=1.67 kHz already described above. The excitation frequencies $f_2$ and $f_1$ of a level pair $\{L_1, L_2\}$ are preferably linked via a frequency ratio of about $f_2/f_1$=1.2. The subsequence belongs to a number of k subsequences, where k is ≥2 and ≤5. In each subsequence a number of $n_k$ level pairs $\{L_1, L_2\}$ are measured.

The start level $\{L_1^{(1)}, L_2^{(1)}\}$ is changed according to the specified step sizes $\Delta L_1$, $\Delta L_2$ according to the formula $L_1^{(n+1)}=L_1^{(n)}+\Delta L_1' \cos(\varphi)$ and the further formula $L_2^{(n+1)}=L_2^{(n)}-\Delta L_1' \sin(\varphi)$. If a descending flank or no ascending flank is measured in the measured subsequence, the search direction is reversed and $\Delta L_1'=-\Delta L_1'$.

In a third sub-step 123, it is checked whether at least three valid DPOAE were measured. If this check is positive, i.e. three valid DPOAE were measured, the procedure continues to the next sub-step 124. If no three valid DPOAE were measured, then the measurement is repeated, where from the original excitation level $L_1^{(old)}$, $L_2^{(old)}$ a new excitation level $L_1^{(1)}$, $L_2^{(1)}$ is computed according to $$L_2^{(1)}=L_2^{(old)}+L_2' \cos(\varphi),$$

$$L_1^{(1)}=L_1^{(old)}+L_2' \sin(\varphi),$$

In the following fourth sub-step 124, the position of the ridge of the individual function is determined on the basis of the three valid measured values, e.g. by solving a parabolic equation and finding the individual maximum according to the function:

$$L_{dp}'^{(G,1)}=f(L_1^{(1 \cdots 3)}, L_2^{(1 \cdots 3)})$$

Here means $L_{dp}'^{(G, 1)}$ is the point on the estimated ridge of the individual model function whose associated excitation level pair is located on line formed by the level pairs $\{L_1^{(1 \cdots 3)}, L_2^{(1 \cdots 3)}\}$. The position of the ridge of the individual function at the higher excitation levels $L^{(1 \cdots 3)}$ is now already known from substep 124, but the slope of the ridge, i.e. the parameter m, is not.

In the following fifth substep 125 of the second step 120, a second subsequence is measured along the assumed ridge, whereby only one measured value is determined. The measurement is carried out according to the formula $L_1^{(4)}= L_{dp}'^{(G, 1)}-\Delta L_2' \sin(\varphi)$.

Undershoots $L_{dp}'^{(G, 1)}$ a preset limit ($L_{dp,min}'^{(G, 1)}$), this step is executed at higher levels ($\Delta L_2=-L_2$).

The value of the DPOAE ($L_{dp}^{(4)}$) is subsequently used in the sixth substep 126 to determine the individual slope of the ridge, m.

In the sixth substep 126 of the second step 120, the individual slope of the ridge is calculated according to the formula m=f($L_{dp}^{(G, 1)}$, $L_1^{(G, 1)}$, $L_2^{(G, 1)}$, $L_{dp}^{(4)}$, $L_1^{(4)}$, $L_2^{(4)}$). Based on the determined gradient m of the ridge, a start level is now determined $L_{1(5)}$, $L_{2(5)}$ for the third subsequence.

In the seventh substep 127 of the second step 120, the measurements of the third subsequence are now performed across the assumed ridge of the function: A variation of $\Delta L_1'$ in $L_1^{(n+1)}=L_1^{(n)}+\Delta L_1' \cos(\varphi)$.

Preferably, at least half of the level pairs $\{L_1, L_2\}$ at which the measurement is performed, are positioned by at least 5 dB on both sides away from the group of the level pairs $\{L_1^{(G)}, L_2^{(G)}\}$ associated with the ridge (of the model function).

With the measured values determined in accordance with the second step 120 and its substeps 121 to 127, the model function already presented is now fitted to the measured values obtained in a third step 130 in the computer unit 10. Here, the three-dimensional model function $p_{dp,M}=f(L_1, L_2)$ is fitted to the measured DPOAE values. The fitting is carried out with the mathematical methods of the regression calculation, e.g. with the least squares method, i.e. with the iterative minimization of the difference between the n measured values and the values of the model function $p_{dp,M}=f (L_1, L_2)$ to the measured n DPOAE (corresponding to the associated $L_1$, $L_2$-coordinates) until an individual function $p_{dp,J}=f(L_1, L_2)$ is obtained with individual parameters of a DPOAE function and level map of the individual by the computer unit 10. Thus an individual function/level map of the hearing of an individual can be easily obtained with greatly reduced measuring effort in a short time.

In a fourth step 140, the output of the individually fitted function and its function parameters takes place in an output device 11 of system 1, such as a display, monitor, printer, etc. The output function parameters contain in particular the parameters already described above: a; b; c; $L_{2,edpt}'$ and the slope of the ridge m. The output medium 11 can, as already mentioned, also be implemented in the form of an interface, via which an external output device, such as a printer or a monitor, can be connected to System 1.

In a possible further process step, the determined individual function of a DPOAE level map and its parameters can be stored by the computer unit 10 in the non-volatile memory 16. The measured raw data from the computer unit 10 can also be stored in the non-volatile memory 16. The stored data can be used by the computer unit 10, e.g. for the continuous extension of the data set underlying the model function of a level map.

The following findings can be gained from the individually adapted function obtained and the associated function parameters:

An approximate distortion product threshold can be calculated which provides information about the threshold of the input signal for the inner hair cells of the measured ear. The corresponding parameter is $L_{2,edpt}$.

The width of the ridge, in the function defined by the parameter c is a measure for the compression and thus for the frequency resolution of the underlying travelling waves in the measured ear.

The position and angle, expressed in function by the parameters a; b contains information about the nature of a hearing loss: In a pure conductive loss, the angle (expressed in function by the parameter a) does not change, instead the hill shifts in the first approximation to the same extent in the direction of higher $L_1$- and $L_2$-Level. If, for example, the displacement of the hill (relative to the standard values, or relative to a reference measurement of the individual at an earlier point in time) coincides with the deterioration of the distortion product threshold, i.e. $\Delta L_2 \approx \Delta L_1 \approx \Delta L_{2,edpt}$ can be inferred from a pure sound conduction loss.

The slope of the ridge, expressed by the parameter m allows conclusions to be drawn about a possible sound-conduction loss. As long as the hearing loss is below 30 dB, it can be expected that the slope of a pure conductive loss corresponds to the standard values, while a deviation from the standard value indicates in a proportional reduction of the retrograde middle-ear transmission at $f_{dp}$.

In an alternative variant of the procedure, instead of the sub-steps 121 to 127, a number of n fixed or predefined but different level pairs $\{L_1, L_2\}$ (where n preferably ≥5 and ≤12, in particular ≥5 and ≤8) is output by the system and the response of an individual's hearing to these level pairs is $\{L_1, L_2\}$ is recorded. This variant can be described as a rigid procedure. The level pairs $\{L_1, L_2\}$ can in turn be used in a number of k subsequences (57, 58; see FIG. 6) are measured, where k≥2 and ≤12 is. The n Level pairs are then largely static and the second and possibly third subsequence are not adapted to the results of the measurements of the first subsequence, as is the case with the procedure described above. The number n of the level pairs $\{L_1, L_2\}$ is designed after weighing the measuring time (as few measuring points as possible) against the achievable accuracy (as many points as possible).

In this rigid procedure with fixed excitation levels, for example with $L_2'=40$ dB for the three higher excitation levels, and $L_2'=25$ dB for the three lower excitation levels, and within a group of three excitation levels, respectively $L_1'=0\pm6$ dB can be measured. In the $\{L_1, L_2\}$-coordinate system, this corresponds to the excitation levels $L_2=68.1$; 65.6; 63.1; 42.8; 45.3; 40.3 and $L_1=68.0$; 73.5; 79.0; 63.3; 57.8; 68.7 (see FIG. 6). The choice of $L_1'=0\pm6$ dB aims at recording three points perpendicular to the presumed position of the ridge, to reliably measure its position: at $f_2=2$ kHz the DPOAE falls with $\Delta L_1'\pm6$ dB typically drops to about 50% of the maximum value. If normal hearing individuals are to be measured first and foremost, as is usually the case with screening tests, the rigid arrangement will give good results. But outliers must be detected. This is possible via the quadratic error of the model adjustment. If the error is too high, i.e. the rms error (rms: root-mean-square) is greater than 5 µPa, for example, further level pairs must be measured until the error is low enough. Here, more $\Delta L_1'$-steps might be suitable. The same procedure must be followed if individual measuring points cannot be registered because the signal-to-noise ratio is too low.

Finally, it should be noted that in deviation from the used and previously described frequency ratio $f_2/f_1$ a different frequency ratio can also be selected instead of 1.2. So the frequency ratio $f_2/f_1$ can be e.g. also another suitable value between 1.15 and 1.35. In addition, the frequency ratio $f_2/f_1$ could be a function of $f_2$.

REFERENCE CHARACTER LIST

1 System
2 Cable connection
3 First line
4 Second line
5 Third line
6 Fourth line
10 computer unit
11 output device
12 AD/DA converter unit
13 DA converter
14 A/D converter
15 Main memory
16 non-volatile memory with stored model function
20 Probe unit, OAE probe
21 First sound output medium, $f_1$-sound generator
22 Second sound output device, $f_2$-sound generator
23 Sound recording medium, microphone
24 Probe tip
30 Ear
31 Ear canal
40 Arrow
51 excitation level pair $\{L_1, L_2\}$
52 excitation level pair $\{L_1, L_2\}$
53 excitation level pair $\{L_1, L_2\}$
54 excitation level pair $\{L_1, L_2\}$
55 excitation level pair $\{L_1, L_2\}$
56 excitation level pair $\{L_1, L_2\}$
57 First subsequence
58 second/further subsequence
70 Graph/Model level map
71 $\{L_1, L_2\}$-map
72 transformed $\{L_1', L_2'\}$-coordinate system
73 ridge (of the DPOAE model level map)
110 First process step
120 Second process step
121 First substep
122 Second substep
12 Third substep
124 Fourt substep
125 Fifth substep
126 sixth substep
127 seventh substep
130 Third process step
140 Fourth process step The procedure described here for the automatic determination of an individual function of a DPOAE level map can be used to avoid errors in the extrapolation of growth functions that may occur in the procedures for measuring the distortion product threshold according to the state-of-the-art described above. In addition, additional data can be obtained, which is then available for diagnosis. In addition to the distortion product threshold Leapt and the slope of the growth function, the procedure described in PCT/EP2017/000334 can also record data on the frequency resolution and compression of the underlying travelling waves and sound conduction loss. It is therefore advantageous to obtain four instead of two informations for the measuring points at the same or even lower expenditure of time, and to reduce estimation errors for the parameters obtained so far (the distortion product threshold Leapt and the slope of the growth function).

In the automatic determination of an individual function of a DPOAE level map described here, the primary tones of each level pair are preferably selected in such a way that both travelling waves at theft-characteristic place have approximately equal amplitudes. Since the $f_1$-travelling wave has not yet reached its maximum at the $f_2$-characteristic place, it is preferably excited much more strongly, at least at moderate overall excitation levels at which the cochlear amplifier is active. However, if the excitation level combination is clearly next to the individually optimal path, the different strength of the travelling waves in the range of $f_2$ may attenuate or intensify the phenomenon shown. Therefore, a combination with the procedure described in PCT/EP2017/000334 can be useful to define an individual function. $p_{dp,I}=f(L_1, L_2)$ with individual parameters of a DPOAE level map.

For a detailed description of the "level map method" please refer to PCT/EP2017/000334.

Objects

The procedure according to the invention is characterized, among other things, by the following objects:

1. A method for detecting distortion products of otoacoustic emissions (DPOAE) in a hearing organ comprising the steps of:
    (a) output of a first primary tone pair $\{f_{1,1}, L_{1,1}, f_{2,1}, L_{2,1}\}$ each comprising a first primary tone with frequency $f_{1,1}$ and sound pressure level $L_{1,1}$ and a second primary tone with frequency $f_{2,1}$ and sound pressure level $L_{2,1}$ with $f_{2,1}>f_{1,1}$, and
    (b) Detection of evoked distortion products of otoacoustic emissions (DPOAE),
    characterized in that the first primary tone $\{f_{1,1}, L_{1,1}\}$ is output with a time delay $t_{lag}$ after the second primary tone $\{f_{2,1}, L_{2,1}\}$.

2. Method according to object 1, characterized in that at least one further primary-tone pair is presented, consisting of a first primary tone with frequency $f_{1,n}$ and sound pressure level $L_{1,n}$ and a second primary tone with frequency $f_{2,n}$ and sound pressure level $L_{2,n}$, where $f_{2,n}>f_{1,n}$.

3. Method according to object 2, characterized in that the second primary tone $\{f_{2,n}, L_{2,n}\}$ of the at least one further n-th primary-tone pair is presented with a time delay $t_{lag}$ after the first primary tone $\{f_{1,n}, L_{1,n}\}$ of this primary-tone pair, the output of the at least one further n-th primary-tone pair $\{f_{1,n}, L_{1,n}, f_{2,n}, L_{2,n}\}$ optionally being presented before or after the presentation of the first primary-tone pair $\{f_{1,1}, L_{1,1}, f_{2,1}, L_{2,1}\}$.

4. Method according to one of the preceding objects, characterized in that the first primary tone $\{f_{1,1}, L_{1,1}\}$ and/or $\{f_{1,n}, L_{1,n}\}$ ("$f_1$-pulse") and optionally the second primary tone $\{f_{2,1}, L_{2,1}\}$ and/or $\{f_{2,n}, L_{2,n}\}$ ("$f_2$-pulse") is presented pulsed.

5. Method according to object 4, characterized in that the pulse length of the $f_1$-pulse of the first primary-tone pair $\{f_{1,1}, L_{1,1}\}$ is shorter than the pulse length of the $f_2$-pulse of the first primary-tone pair $\{f_{2,1}, L_{2,1}\}$, and/or the pulse length of the $f_2$-pulse of the n-th further primary-tone pair $\{f_{2,n}, L_{2,n}\}$ is shorter than the pulse length of the $f_1$-pulse of the n-th further primary-tone pair $\{f_{1,n}, L_{1,n}\}$.

6. Method according to one of the preceding objects, characterized in that the time delay $t_{lag}$ is between 10 ms and 0.1 ms, preferably between 5 ms and 0.5 ms.

7. Method according to one of the preceding objects, characterized in that the duration of the $f_1$-pulse $\{f_{1,1}, L_{1,1}\}$ of the first primary tone pair and/or of the $f_2$-pulse $\{f_{2,n}, L_{2,n}\}$ of the n-th further primary-tone pair is 200 ms or less, 100 ms or less, 50 ms or less, between 40 ms to 1 ms, between 30 ms and 2 ms or between 25 ms and 5 ms.

8. Method according to one of the preceding objects, characterized in that the $f_1$-pulse of the first primary-tone pair $\{f_{1,1}, L_{1,1}; f_{2,1}, L_{2,1}\}$ is switched off after the end of the $f_2$-pulse of the first primary-tone pair.

9. Method according to one of the objects 2 to 8, characterized in that a set consisting of the first primary-tone pair $\{f_{1,1}, L_{1,1}; f_{2,1}, L_{2,1}\}$ and the at least one further primary-tone pair $\{f_{1,n}, L_{1,n}; f_{2,n}, L_{2,n}\}$ is presented in a block which is repeated several times during the measuring period.

10. Method according to any of the foregoing objects, further comprising the automatic determination of an individual function of a DPOAE level map having $p_{dp,I}=f(L_1, L_2)$ to determine the optimal DPOAE excitation level:

Reading a model function $p_{dp,M}=f(L_1, L_2)$ with model parameters of a DPOAE level map, based on a number of N DPOAE measurements of an excitation frequency pair $f_1, f_2$ each with different level pairs $\{L_1^{(1 \cdots N)}, L_2^{(1 \cdots N)}\}$ in a population (p) of subjects with normal hearing, into a working memory of a computer unit, where N≥40 and p≥2, automatic presentation of n different level pairs $\{L_1^{(1 \cdots n)}, L_2^{(1 \cdots n)}\}$ of an excitation frequency pair $f_1, f_2$ via sound output means to an individual and detecting the corresponding DPOAE of the individual via sound recording means, wherein at least the first level pair $\{L_1^{(1)}, L_2^{(1)}\}$ is predefined and where n<<N, iterative fitting of the model function $p_{dp,M}=f(L_1, L_2)$ to the measured n DPOAE until an individual level-map function is obtained $p_{dp,I}=f(L_1, L_2)$ with individual parameters of a DPOAE level map of the individual by the computer unit, Output of the individual function $p_{dp,I}=f(L_1, L_2)$ and/or their individual parameters on an output device of the computer unit.

11. Use the procedure according to one of the previous objects to adjust a hearing aid.

The invention claimed is:

1. A method for detecting distortion products of otoacoustic emissions (DPOAE) in a hearing organ comprising the steps of:
    (a) output of a first primary tone pair $\{f_{1,1}, L_{1,1}, f_{2,1}, L_{2,1}\}$ each comprising a first primary tone with frequency $f_{1,1}$ and sound pressure level $L_{1,1}$ and a second primary tone with frequency $f_{2,1}$ and sound pressure level $L_{2,1}$ with $f_{2,1}>f_{1,1}$, and
    (b) detection of evoked distortion products of otoacoustic emissions (DPOAE), wherein the first primary tone $\{f_{1,1}, L_{1,1}\}$ is output with a time delay tag after the second primary tone $\{f_{2,1}, L_{2,1}\}$, wherein at least one further primary-tone pair is presented, consisting of a first primary tone with frequency $f_{1,n}$ and sound pressure level $L_{1,n}$ and a second primary tone with frequency $f_{2,n}$ and sound pressure level $L_{2,n}$ where $f_{2,n} > f_{1,n}$, wherein the second primary tone $\{f_{2,n}, L_{2,n}\}$ of the at least one further n-th primary-tone pair has a time delay tag after the first primary tone $\{f_{1,n}, L_{1,n}\}$ of this primary-tone pair, wherein $\{f_{1,1}, L_{1,1}\} = \{f_{1,n}, L_{1,n}\}$ and $\{f_{2,1}, L_{2,1}\} = \{f_{2,n}, L_{2,n}\}$, and wherein the method further comprises a step of comparing the DPOAE evoked by output of the first primary-tone pair $\{f_{1,1}, L_{1,1}, f_{2,1}, L_{2,1}\}$ with the DPOAE evoked by the output of each n-th further primary-tone pair $\{f_{1,n}, L_{1,n}, f_{2,n}, L_{2,n}\}$.

2. The method according to claim 1, wherein the output of the at least one further n-th primary-tone pair $\{f_{1,n}, L_{1,n}, f_{2,n}, L_{2,n}\}$ takes place before or after the output of the first primary-tone pair $\{f_{1,1}, L_{1,1}, f_{2,1}, L_{2,1}\}$.

3. The method according to claim 1, where n=2.

4. The method according to claim 1, wherein the first primary tone $\{f_{1,1}, L_{1,1}\}$ and/or $\{f_{1,n}, L_{1,n}\}$ ("$f_1$-pulse") and optionally the second primary tone $\{f_{2,1}, L_{2,1}\}$ and/or $\{f_{2,n}, L_{2,n}\}$ ("$f_2$-pulse") can be presented pulsed.

5. The method according to claim 4, wherein a pulse length of the $f_1$-pulse of the first primary-tone pair $\{f_{1,1}, L_{1,1}\}$ is shorter than a pulse length of the $f_2$-pulse of the first primary-tone pair $\{f_{2,1}, L_{2,1}\}$, and/or a pulse length of the $f_2$-pulse of the n-th further primary-tone pair $\{f_{2,n}, L_{2,n}\}$ is shorter than a pulse length of the $f_1$-pulse of the n-th further primary tone pair $\{f_{1,n}, L_{1,n}\}$.

6. The method according to claim 4, wherein the $f_1$-pulse of the first primary-tone pair $\{f_{1,1}, L_{1,1}; f_{2,1}, L_{2,1}\}$ is switched off before or after the end of the $f_2$-pulse of the first primary-tone pair.

7. The method according to claim 1, wherein the time delay tag is between 10 ms and 0.1 ms or between 5 ms and 0.5 ms.

8. The method according claim 1, wherein a duration of the $f_1$-pulse of the first and optionally each further n-th primary-tone pair and/or a duration of the $f_2$-pulse of the first and optionally each further n-th primary-tone pair is selected to be greater than a latency of the evoked DPOAE, or at least twice, or at least three times or at least five times as long.

9. The method according to claim 1, wherein a duration of the first primary tone $\{f_{1,1}, L_{1,1}\}$ of the first primary tone pair and/or of the second primary tone $\{f_{2,n}, L_{2,n}\}$ of the n-th further primary-tone pair is 200 ms or less, 100 ms or less, 50 ms or less, between 40 ms to 1 ms, between 30 ms and 2 ms or between 25 ms and 5 ms.

10. The method according to claim 1, wherein a set of the first primary-tone pair $\{f_{1,1}, L_{1,1}; f_{2,1}, L_{2,1}\}$ and the at least one further primary tone pair $\{f_{1,n}, L_{1,n}; f_{2,n}, L_{2,n}\}$ is output in a block which is repeated several times during a measurement period.

11. The method according to claim 10, wherein in a block a beginning of a primary-tone pair follows a beginning of the primary-tone pair immediately preceding in the block with a time interval $T_a$, where $T_a$ is >10 ms.

12. The method according to claim 10, wherein in a block second excitation frequencies $f_2$ of two immediately successive pairs of primary tones are at least one octave apart.

13. The method according to claim 10, wherein during the measurement period measured sound pressure levels of the DPOAE are averaged for primary-tone pairs of same second excitation frequencies $f_2$.

14. The method according to claim 10, wherein the or each block of primary-tone pairs is presented during a block time selected such that there is a time interval of 30 ms to 100 ms, or at least 70 ms, between a beginning of a first and a subsequent primary-tone pair with same excitation frequencies $f_2$.

15. The method according to claim 10, wherein sound pressure levels of the DPOAE are measured and averaged for all second excitation frequencies $f_2$ contained in a or each set at a second sound pressure level $L_2$ respectively associated with an excitation frequency $f_2$, and measurements of sound pressure levels of the DPOAE are performed at least once for new sound pressure levels $L_2$.

16. The method according to claim 1, wherein a duration of the first and second primary tones of each pair of primary tones is between 2 ms and 20 ms.

17. The method according to claim 1, wherein at a beginning of measurements it is checked whether a frequency $f_{dp}$ of one of the DPOAEs interferes with a spontaneous emission (SOAE).

18. The method according to claim 1, further comprising automatically determining an individual function of a DPOAE level map having $p_{dp,I} = f(L_1, L_2)$ to determine an optimal DPOAE excitation level:

Reading a model function $p_{dp,M} = f(L_1, L_2)$ with model parameters of a DPOAE level chart, based on a number of N DPOAE measurements of an excitation frequency pair $f_1$, $f_2$ each with different level pairs $\{L_1^{(1 \cdots N)}, L_2^{(1 \cdots N)}\}$ in a population (p) of subjects with normal hearing, into a working memory of a computer unit, where $N \geq 40$ and $p \geq 2$, automatic presentation of n different level pairs $\{L_1^{(1 \cdots n)}, L_2^{(1 \cdots n)}\}$ of an excitation frequency pair $f_1$, $f_2$ via sound output means to an individual and detecting a corresponding DPOAE of the individual via sound recording means, wherein at least a first level pair $\{L_1^{(1)}, L_2^{(1)}\}$ is predefined and where n<<N, iterative fitting of a model level-map function $p_{dp,M} = f(L_1, L_2)$ to measured n DPOAE until an individual function is obtained $p_{dp,I} = f(L_1, L_2)$ with individual parameters of a DPOAE level map of the individual by the computer unit, output of the individual function $p_{dp,I} = f(L_1, L_2)$ and/or their individual parameters on an output device of the computer unit.

19. The method according to claim 18, wherein the model function has an approximately linearly increasing ridge (73) which is approximately linearly related to $\{L_1^{(G)}, L_2^{(G)}\}$ level pairs, at least half of measured level pairs $\{L_1, L_2\}$ being at least 5 dB on both sides away from the group of signals evoked by the level pairs $\{L_1^{(G)}, L_2^{(G)}\}$ associated with the ridge (73).

* * * * *

UNITED STATES PATENT AND TRADEMARK OFFICE
CERTIFICATE OF CORRECTION

PATENT NO. : 11,786,149 B2  
APPLICATION NO. : 16/623091  
DATED : October 17, 2023  
INVENTOR(S) : Ernst Dalhoff et al.

Page 1 of 1

It is certified that error appears in the above-identified patent and that said Letters Patent is hereby corrected as shown below:

In the Specification

Column 7, Line 25, the text reading "delay tlag" should read -- delay $t_{lag}$ --

In the Claims

Column 26, Line 66 (Claim 1, Line 11), the text reading "delay tag" should read -- delay $t_{lag}$ --

Column 27, Line 7 (Claim 1, Line 19), the text reading "delay tag" should read -- delay $t_{lag}$ --

Column 27, Line 37 (Claim 7, Line 2), the text reading "delay tag" should read -- delay $t_{lag}$ --

Signed and Sealed this  
Fifth Day of March, 2024

Katherine Kelly Vidal  
*Director of the United States Patent and Trademark Office*